United States Patent
Keranen et al.

(10) Patent No.: US 10,241,017 B2
(45) Date of Patent: Mar. 26, 2019

(54) HIGH TEMPERATURE HEATING SYSTEM

(71) Applicant: Bruker Nano, Inc., Santa Barbara, CA (US)

(72) Inventors: Lucas Paul Keranen, Hutchinson, MN (US); Syed Amanulla Syed Asif, Bloomington, MN (US); Ryan Major, Crystal, MN (US); Yunje Oh, Medina, MN (US)

(73) Assignee: Bruker Nano, Inc., Santa Barbara, CA (US)

( * ) Notice: Subject to any disclaimer, the term of this patent is extended or adjusted under 35 U.S.C. 154(b) by 353 days.

(21) Appl. No.: 14/361,094

(22) PCT Filed: Nov. 28, 2012

(86) PCT No.: PCT/US2012/066846
§ 371 (c)(1),
(2) Date: May 28, 2014

(87) PCT Pub. No.: WO2013/082148
PCT Pub. Date: Jun. 6, 2013

(65) Prior Publication Data
US 2014/0331782 A1 Nov. 13, 2014

Related U.S. Application Data

(60) Provisional application No. 61/564,188, filed on Nov. 28, 2011.

(51) Int. Cl.
*G01N 3/54* (2006.01)
*G01N 3/18* (2006.01)
(Continued)

(52) U.S. Cl.
CPC ............ *G01N 3/54* (2013.01); *G01N 3/08* (2013.01); *G01N 3/18* (2013.01); *H05B 1/023* (2013.01);
(Continued)

(58) Field of Classification Search
CPC ...................................................... G01N 3/54
(Continued)

(56) References Cited

U.S. PATENT DOCUMENTS 2,535,830 A    12/1950  Beck
3,028,754 A *   4/1962  Huyser .............. G01B 5/30
                                                    33/787
(Continued)

FOREIGN PATENT DOCUMENTS

EP         0855452 A1    7/1998
EP      2011066018 A1    6/2011
(Continued)

OTHER PUBLICATIONS

"U.S. Appl. No. 13/510,825, Examiner Interview Summary dated Nov. 18, 2014", 3 pgs.
(Continued)

*Primary Examiner* — Robert R Raevis
(74) *Attorney, Agent, or Firm* — Schwegman Lundberg & Woessner, P.A.

(57) ABSTRACT

A sample gripping and heating assembly includes an assembly housing and first and second heating grips coupled with the assembly housing. The first and second heating grips each include a gripping surface, and the gripping surfaces of the first and second heating grips are opposed to each other. Each of the first and second heating grips further includes a heating element adjacent to the gripping surface. Optionally, the sample gripping and heating assembly is included in a heating system including a probe heater having a probe
(Continued)

heating element for heating of a probe. The heating system is included with a testing assembly having a stage coupled with the sample gripping and heating assembly, and a transducer assembly coupled with the probe heater.

15 Claims, 7 Drawing Sheets

(51) Int. Cl.
  *G01N 3/08* (2006.01)
  *H05B 1/02* (2006.01)
  *H05B 3/32* (2006.01)

(52) U.S. Cl.
  CPC ....... *H05B 3/32* (2013.01); *G01N 2203/0078* (2013.01); *G01N 2203/0226* (2013.01); *G01N 2203/0282* (2013.01); *G01N 2203/0286* (2013.01); *G01N 2203/0482* (2013.01)

(58) Field of Classification Search
  USPC .............................. 73/818–825; 374/51, 52
  See application file for complete search history.

(56) References Cited

U.S. PATENT DOCUMENTS

| | | | |
|---|---|---|---|
| 3,896,314 A | 7/1975 | Nukuri et al. | |
| 4,346,754 A | 8/1982 | Imig et al. | |
| 4,474,015 A | 10/1984 | Christmas et al. | |
| 4,491,788 A | 1/1985 | Zandonatti | |
| 4,703,181 A | 10/1987 | Swann et al. | |
| 4,735,092 A * | 4/1988 | Kenny | G01N 3/18 |
| | | | 73/840 |
| 4,820,051 A | 4/1989 | Yanagisawa et al. | |
| 4,917,462 A | 4/1990 | Lewis et al. | |
| 4,992,660 A | 2/1991 | Kobayashi | |
| 4,996,433 A | 2/1991 | Jones et al. | |
| 5,015,825 A * | 5/1991 | Brindley | F27B 17/02 |
| | | | 219/390 |
| 5,202,542 A | 4/1993 | Ferguson | |
| 5,331,134 A | 7/1994 | Kimura | |
| 5,367,171 A | 11/1994 | Aoyama et al. | |
| 5,507,189 A | 4/1996 | Kim et al. | |
| 5,512,727 A | 4/1996 | Myers et al. | |
| 5,553,486 A | 9/1996 | Bonin | |
| 5,654,546 A | 8/1997 | Lindsay | |
| 5,661,235 A | 8/1997 | Bonin | |
| 5,731,587 A | 3/1998 | Dibattista et al. | |
| 5,821,545 A | 10/1998 | Lindsay et al. | |
| 5,869,751 A | 2/1999 | Bonin | |
| 6,026,677 A | 2/2000 | Bonin | |
| 6,339,958 B1 | 1/2002 | Tsui et al. | |
| 6,495,838 B1 | 12/2002 | Yaguchi et al. | |
| 6,520,004 B1 | 2/2003 | Lin | |
| 6,840,305 B2 | 1/2005 | Zheng et al. | |
| 7,274,450 B1 | 9/2007 | Green | |
| 7,451,636 B2 | 11/2008 | Bradshaw et al. | |
| 7,674,037 B2 | 3/2010 | Liu et al. | |
| 7,685,868 B2 | 3/2010 | Woirgard et al. | |
| 7,685,869 B2 | 3/2010 | Bonilla et al. | |
| 7,798,011 B2 | 9/2010 | Warren et al. | |
| 7,878,071 B2 | 2/2011 | Greer | |
| 8,042,405 B2 | 10/2011 | Shuaib et al. | |
| 8,065,929 B2 | 11/2011 | Yakimoski et al. | |
| 8,161,803 B2 | 4/2012 | Oh et al. | |
| 8,434,370 B2 | 5/2013 | Oh et al. | |
| 8,474,324 B2 | 7/2013 | Rihan et al. | |
| 8,479,589 B2 | 7/2013 | Shuaib et al. | |
| 8,569,714 B2 | 10/2013 | Han et al. | |
| 8,631,687 B2 | 1/2014 | Patten et al. | |
| 8,844,368 B2 | 9/2014 | Peecock et al. | |
| 9,189,592 B2 | 11/2015 | Nam et al. | |
| 9,316,569 B2 | 4/2016 | Oh et al. | |
| 9,476,816 B2 | 10/2016 | Schmitz et al. | |
| 9,759,641 B2 | 9/2017 | Oh et al. | |
| 9,804,072 B2 | 10/2017 | Asif et al. | |
| 9,829,417 B2 | 11/2017 | Schmitz et al. | |
| 2002/0110177 A1 | 8/2002 | Nakayama et al. | |
| 2003/0140684 A1 | 7/2003 | Broz et al. | |
| 2006/0025002 A1 | 2/2006 | Zhang et al. | |
| 2006/0180577 A1 | 8/2006 | Lindeman | |
| 2007/0180924 A1 | 8/2007 | Warren et al. | |
| 2007/0193347 A1 | 8/2007 | Bradshaw et al. | |
| 2007/0278420 A1 | 12/2007 | Molhave | |
| 2008/0092938 A1 | 4/2008 | Majumdar et al. | |
| 2008/0169428 A1 | 7/2008 | Schoenlein | |
| 2008/0266653 A1 | 10/2008 | Korpinen et al. | |
| 2008/0276727 A1 | 11/2008 | Enoksson et al. | |
| 2008/0290290 A1 | 11/2008 | Nagakubo et al. | |
| 2009/0044679 A1 | 2/2009 | Sawa et al. | |
| 2009/0111701 A1 | 4/2009 | Ahn et al. | |
| 2009/0120172 A1 | 5/2009 | Bradshaw et al. | |
| 2009/0194689 A1 | 8/2009 | Abramson et al. | |
| 2009/0206258 A1 | 8/2009 | Kasai et al. | |
| 2009/0289050 A1 | 11/2009 | Ondricek | |
| 2010/0095780 A1 | 4/2010 | Oh et al. | |
| 2010/0107745 A1 | 5/2010 | Bonin | |
| 2010/0132441 A1 | 6/2010 | Oh et al. | |
| 2010/0180356 A1 | 7/2010 | Bonilla et al. | |
| 2010/0186520 A1 | 7/2010 | Wheeler, IV et al. | |
| 2010/0212411 A1 | 8/2010 | Passilly et al. | |
| 2010/0225037 A1* | 9/2010 | Adldinger | B21D 53/02 |
| | | | 269/287 |
| 2010/0294147 A1 | 11/2010 | Loiret-bernal et al. | |
| 2011/0107472 A1 | 5/2011 | Han et al. | |
| 2011/0152724 A1 | 6/2011 | Hansma et al. | |
| 2011/0252874 A1 | 10/2011 | Patten et al. | |
| 2011/0277555 A1 | 11/2011 | Peecock et al. | |
| 2011/0277556 A1 | 11/2011 | Peecock et al. | |
| 2012/0292528 A1 | 11/2012 | Oh et al. | |
| 2013/0098145 A1 | 4/2013 | Oh et al. | |
| 2014/0293293 A1 | 10/2014 | Vodnick et al. | |
| 2014/0326707 A1 | 11/2014 | Schmitz et al. | |
| 2015/0033835 A1 | 2/2015 | Asif et al. | |
| 2015/0179397 A1 | 6/2015 | Damiano, Jr. et al. | |
| 2015/0185117 A1 | 7/2015 | Schmitz | |
| 2016/0123859 A1 | 5/2016 | Oh et al. | |

FOREIGN PATENT DOCUMENTS

| | | |
|---|---|---|
| EP | 2861934 A | 4/2015 |
| EP | 2780689 B1 | 1/2017 |
| EP | 2861934 B1 | 5/2017 |
| GB | 2116459 A | 9/1993 |
| JP | 4996867 A | 12/1972 |
| JP | 4996867 U | 8/1974 |
| JP | 5588256 A | 7/1980 |
| JP | 55088256 A | 7/1980 |
| JP | 5691598 A | 7/1981 |
| JP | 57201953 A | 12/1982 |
| JP | 6327731 A | 3/1983 |
| JP | 58173159 A | 10/1983 |
| JP | 58173159 U | 11/1983 |
| JP | 5915635 A | 1/1984 |
| JP | 570201953 | 5/1984 |
| JP | 60127540 A | 7/1985 |
| JP | 60127540 U | 12/1986 |
| JP | 181553 U | 5/1989 |
| JP | 01081553 U | 5/1989 |
| JP | 01119153 A | 5/1989 |
| JP | 0366122 A | 3/1991 |
| JP | 04131741 A | 5/1992 |
| JP | 0566186 A | 3/1993 |
| JP | 0572457 A | 3/1993 |
| JP | 06315299 A | 11/1994 |
| JP | 2000241325 A | 9/2000 |
| JP | 2000241332 A | 9/2000 |
| JP | 2000314692 A | 11/2000 |
| JP | 2002116130 A | 4/2002 |
| JP | 2002318318 A | 10/2002 |
| JP | 2006526775 A | 11/2006 |
| JP | 2008512841 A | 4/2008 |
| JP | 2008134191 A | 6/2008 |

(56) References Cited

FOREIGN PATENT DOCUMENTS

| JP | 2008197000 A | 8/2008 |
|---|---|---|
| JP | 2009526230 A | 7/2009 |
| JP | 2009193833 A | 8/2009 |
| JP | 2013512545 A | 4/2013 |
| JP | 2015501935 A | 1/2015 |
| JP | 6162770 | 6/2017 |
| JP | 6247331 B2 | 12/2017 |
| WO | WO-2008061224 | 5/2008 |
| WO | WO-2011066018 A1 | 6/2011 |
| WO | WO-2011104529 A1 | 9/2011 |
| WO | WO-2013074623 A1 | 5/2013 |
| WO | WO-2013082145 A1 | 6/2013 |
| WO | WO-2013082148 A1 | 6/2013 |
| WO | WO-2013187972 A1 | 12/2013 |

OTHER PUBLICATIONS

"U.S. Appl. No. 13/510,825, Final Office Action dated Dec. 26, 2014", 17 pgs.
"U.S. Appl. No. 13/510,825, Notice of Allowance dated Aug. 28, 2015", 8 pgs.
"U.S. Appl. No. 14/358,065, Final Office Action dated Nov. 18, 2015", 10 pgs.
"U.S. Appl. No. 14/358,065, Response filed Oct. 28, 2015 to Non Final Office Action dated Jul. 31, 2015", 12 pgs.
"European Application Serial No. 12853965.7, Extended European Search Report dated Nov. 16, 2015", 10 pgs.
"Japanese Application Serial No. 2015-517243, Final Office Action dated Dec. 1, 2015", W/ English Translation, 5 pgs.
"U.S. Appl. No. 13/510,825, Notice of Allowance dated Jan. 29, 2016", 7 pgs.
"U.S. Appl. No. 14/948,549, Preliminary Amendment filed Jan. 14, 2016", 9 pgs.
"European Application Serial No. 12853899.8, Response filed Jan. 26, 2016 to Extended European Search Report dated Jun. 29, 2015", 12 pgs.
"U.S. Appl. No. 13/510,825, Non Final Office Action dated Jun. 3, 2014", 28 pgs.
"U.S. Appl. No. 13/510,825, Preliminary Amendment filed May 18, 2012", 3 pgs.
"U.S. Appl. No. 14/358,065, Preliminary Amendment filed May 14, 2014", 8 pgs.
"U.S. Appl. No. 14/361,133, Preliminary Amendment filed May 28, 2014", 8 pgs.
"Application Serial No. PCT/US2012/065009, Article 19 Amendment filed Mar. 25, 2013", 6 pgs.
"European Application Serial No. 10833722.1, Preliminary Amendment filed Jan. 21, 2013", 21 pgs.
"International Application Serial No. PCT/US2012/065009, Supplemental Article 19 Amendment filed Apr. 26, 2013", 12 pgs.
"International Application Serial No. PCT/US2012/065009, International Preliminary Report on Patentability dated May 30, 2014", 7 pgs.
"International Application Serial No. PCT/US2012/066842, Demand and Response filed Sep. 27, 2013 to Written Opinion dated Feb. 7, 2013", 25 pgs.
"International Application Serial No. PCT/US2012/066842, International Preliminary Report on Patentability dated Jun. 12, 2014", 10 pgs.
"International Application Serial No. PCT/US2012/066846, Demand and Response filed Sep. 27, 2013 to Written Opinion dated Feb. 6, 2013", 26 pgs.
"U.S. Appl. No. 14/358,065, Notice of Allowance dated Jun. 14, 2016", 9 pgs.
"U.S. Appl. No. 14/361,133, Final Office Action dated Nov. 3, 2016", 13 pgs.
"U.S. Appl. No. 14/361,133, Response filed Oct. 12, 2016 to Non Final Office Action dated Apr. 15, 2016", 15 pgs.
"U.S. Appl. No. 14/407,783, Final Office Action dated Sep. 23, 2016", 8 pgs.
"U.S. Appl. No. 14/407,783, Response filed Sep. 16, 2016 to Non Final Office Action dated Mar. 16, 2016", 15 pgs.
"U.S. Appl. No. 14/948,549, Non Final Office Action dated Oct. 26, 2016", 8 pgs.
"European Application Serial No. 12853899.8, Office Action dated May 30, 2016", 8 pgs.
"European Application Serial No. 12853965.7, Communication Pursuant to Article 94(3) EPC dated Oct. 13, 2016", 3 pgs.
"European Application Serial No. 12853965.7, Response filed Jun. 8, 2016 to Extended European Search Report dated Nov. 16, 2015", 17 pgs.
"European Application Serial No. 13804048.0, Response filed Sep. 7, 2016 to Extended European Search Report dated Feb. 9, 2016", 39 pgs.
"Japanese Application Serial No. 2014-543623, Office Action dated Oct. 4, 2016", W/ English Translation, 10 pgs.
"Japanese Application Serial No. 2014-543624, Office Action dated Oct. 4, 2016", W/ English Translation, with English Translation, 9 pgs.
"Japanese Application Serial No. 2015-202642, Office Action dated Sep. 6, 2016", W/ English Translation, 4 pgs.
"U.S. Appl. No. 14/407,783, Notice of Allowance dated Mar. 10, 2017", 6 pgs.
"U.S. Appl. No. 14/407,783, Notice of Allowance dated Mar. 29, 2017", 6 pgs.
"U.S. Appl. No. 14/407,783, Response filed Feb. 23, 2017 to Final Office Action dated Sep. 23, 2016", 15 pgs.
"U.S. Appl. No. 14/948,549, Notice of Allowance dated Mar. 22, 2017", 12 pgs.
"European Application Serial No. 12853899.8, Response filed Dec. 9, 2016 to Office Action dated May 30, 2016", 15 pgs.
"European Application Serial No. 12853965.7, Response filed Feb. 16, 2017 to Communication Pursuant to Article 94(3) EPC dated Oct. 13, 2016", 12 pgs.
"Japanese Application Serial No. 2014543623, Response filed Mar. 3, 2017 to Office Action dated Oct. 4, 2016", w/English Translation, 12 pgs.
"Japanese Application Serial No. 2015-202642, Response filed Dec. 5, 2016 to Office Action dated Sep. 6, 2016", W/ English Claims, 8 pgs.
"Japanese Application Serial No. 2016-074111, Office Action dated Dec. 12, 2016", w/English Translation, 6 pgs.
"Japanese Application Serial No. 2014-543623, Response filed Dec. 22, 2017 to Examiners Decision of Final Refusal dated Aug. 22, 2017", w. English Translation, 17 pgs.
"Japanese Application Serial No. 2014-543624, Office Action dated Jan. 16, 2018", w. English Claims, 5 pgs.
"Japanese Application Serial No. 2014-543624, Response filed Dec. 22, 2017 to Examiners Decision of Final Refusal dated Aug. 22, 2017", w. English Translation, 6 pgs.
"U.S. Appl. No. 14/361,133, Corrected Notice of Allowance dated Aug. 14, 2017", 4 pgs.
"U.S. Appl. No. 14/361,133, Corrected Notice of Allowance dated Oct. 5, 2017", 4 pgs.
"U.S. Appl. No. 14/407,783, Notice of Allowance dated Jul. 21, 2017", 5 pgs.
"U.S. Appl. No. 14/948,549, PTO Response to Rule 312 Communication dated Aug. 14, 2017", 2 pgs.
"European Application Serial No. 10833722.1, Extended European Search Report dated Oct. 9, 2017", 10 pgs.
"European Application Serial No. 12853899.8, Response filed Sep. 27, 2017 to Communication Pursuant to Article 94(3) EPC dated Mar. 17, 2017", 13 pgs.
"Japanese Application Serial No. 2014-543623, Examiners Decision of Final Refusal dated Aug. 22, 2017", With English Translation, 6 pgs.
"Japanese Application Serial No. 2014-543624, Examiners Decision of Final Refusal dated Aug. 22, 2017", with English Translation, 6 pgs.

(56) References Cited

OTHER PUBLICATIONS

"Japanese Application Serial No. 2016-074111, Response filed Aug. 1, 2017 to Office Action dated Dec. 12, 2016", with English Translation, 20 pgs.
"U.S. Appl. No. 14/361,133, Notice of Allowance dated Jun. 5, 2017", 9 pgs.
"U.S. Appl. No. 14/361,133, Response filed May 3, 2017 to Final Office Action dated Nov. 3, 2016", 13 pgs.
"European Application Serial No. 12853899.8, Communication Pursuant to Article 94(3) EPC dated Mar. 17, 2017", 7 pgs.
"Japanese Application Serial No. 2014-543623, Office Action dated Mar. 20, 2018", w/ English translation, 11 pgs.
"Japanese Application Serial No. 2014-543623, Response filed Jun. 13, 2018 to Office Action dated Mar. 20, 2018", 3 pgs.
"Japanese Application Serial No. 2014-543623, Notification of Release of Application from Zenchi Examination dated Jun. 29, 2018", w/o Translation, 5 pgs.
"Japanese Application Serial No. 2014-543623, Response filed Jul. 25, 2018 to Notification of Release of Application from Zenchi Examination dated Jun. 29, 2018", 2 pgs.
"U.S. Appl. No. 13/090,036, Notice of Allowance dated Mar. 19, 2013", 8 pgs.
"U.S. Appl. No. 13/090,036, Notice of Allowance dated Jul. 15, 2013", 9 pgs.
"U.S. Appl. No. 13/510,825 , Response filed Jun. 27, 2013 to Non Final Office Action dated Mar. 27, 2013", 30 pgs.
"U.S. Appl. No. 13/510,825, Examiner Interview Summary dated Jul. 10, 2013", 3 pgs.
"U.S. Appl. No. 13/510,825, Final Office Action dated Aug. 27, 2013", 26 pgs.
"U.S. Appl. No. 13/510,825, Non Final Office Action dated Mar. 27, 2013", 14 pgs.
"U.S. Appl. No. 13/510,825, Response filed Nov. 26, 2013 to Final Office Action dated Aug. 27, 2013", 34 pgs.
"International Application Serial No. PCT/US2010/046865, International Preliminary Report on Patentability dated May 30, 2012", 10 pgs.
"International Application Serial No. PCT/US2010/046865, Search Report dated Oct. 28, 2010", 2 pgs.
"International Application Serial No. PCT/US2010/046865, Written Opinion dated Oct. 28, 2010", 8 pgs.
"International Application Serial No. PCT/US2012/065009, International Search Report dated Jan. 25, 2013", 2 pgs.
"International Application Serial No. PCT/US2012/065009, Written Opinion dated Jan. 25, 2013", 5 pgs.
"International Application Serial No. PCT/US2012/066842, International Preliminary Report on Patentability dated Dec. 6, 2013", 15 pgs.
"International Application Serial No. PCT/US2012/066842, International Search Report dated Feb. 7, 2013", 2 pgs.
"International Application Serial No. PCT/US2012/066842, Written Opinion dated Feb. 7, 2013", 8 pgs.
"International Application Serial No. PCT/US2012/066846, International Preliminary Report on Patentability dated Dec. 3, 2013", 16 pgs.
"International Application Serial No. PCT/US2012/066846, International Search Report dated Feb. 6, 2013", 2 pgs.
"International Application Serial No. PCT/US2012/066846, Written Opinion dated Feb. 6, 2013", 8 pgs.
"International Application Serial No. PCT/US2013/031650, International Search Report dated May 31, 2013", 2 pgs.
"International Application Serial No. PCT/US2013/031650, Written Opinion dated May 31, 2013", 4 pgs.
"Japanese Application Serial No. 2012-541077, Office Action dated Mar. 18, 2014", 4 pgs.
Allard, L. F., et al., "A New Paradigm for Ultra-High-Resolution Imaging at Elevated Temperatures", Microscopy and Microanalysis, 14(Supp. S2), (2008), 792-793.

Briceno, M., et al., "In-situ TEM Observations on the Sintering Process of Colloidal Gold Using an Ultra-fast Heating Stage", Microscopy and Microanalysis, 14(Suppl 2), (2008), 1336-1337.
Damiano, John, et al., "A MEMS-based Technology Platform for in-situ TEM Heating Studies", Microscopy and Microanalysis, 14(Suppl 2), (2008), 1332-1333.
Eakins, D. E., et al., "An in situ TEM study of phase formation in gold-aluminum couples", Journal of Materials Science, 39, (2004), 165-171.
Kamino, T., et al., "A newly developed high resolution hot stage and its application to materials characterization", Microsc. Microanal. Microstruct., 4, (1993), 127-135.
Kamino, T., et al., "In-situ high-resolution electron microscopy study on a surface reconstruction of Au-deposited Si at very high temperatures", Philosophical Magazine A, 75(1), (1997), 105-114.
Min, K.-H., et al., "Crystallization behaviour of ALD-Ta2O5 thin films: the application of in-situ TEM", Philosophical Magazine, 85(18), (Jun. 21, 2005), 2049-2063.
Saka, H., "In situ observation of solid-liquid interfaces by transmission electron microscopy", J. Mater. Res., 20(7), (Jul. 2005), 1629-1640.
Saka, H., "In-situ TEM observation of transformation of dislocations from shuffle to glide sets in Si under supersaturation of interstitials", Philosophical Magazine, 86(29-31), (Oct.-Nov. 2006), 4841-4850.
Tsukimoto, S., et al., "In situ high resolution electron microscopy/ electron energy loss spectroscopy observation of wetting of a Si surface by molten Al", Journal of Microscopy, 203(Pt 1), (Jul. 2001), 17-21.
Wu, Yiying, et al., "Direct Observation of Vapor-Liquid-Solid Nanowire Growth", J. Am. Chem. Soc., 123, (Mar. 13, 2001), 3165-3166.
U.S. Appl. No. 13/510,825, filed Jul. 30, 2012, Micro Electro-Mechanical Heater.
U.S. Appl. No. 13/090,036, filed Apr. 19, 2011, Indenter Assembly.
U.S. Appl. No. 14/358,065, filed May 14, 2014, Probe Tip Heating Assembly.
U.S. Appl. No. 14/361,133, filed May 28, 2014, High Temperature Heating System.
"European Application Serial No. 12853899.8, Communication Pursuant to Article 94(3) EPC dated Oct. 24, 2018", 9 pgs.
"Japanese Application Serial No. 2014-543623 Final Office Action dated Oct. 30, 2018", w/ Concise Statement of Relevance, (Oct. 30, 2018), 9 pgs.
"Japanese Application Serial No. 2014-543624, Office Action dated Oct. 23, 2018", w/ Concise Statement of Relevance, 9 pgs.
"U.S. Appl. No. 13/510,825, Corrected Notice of Allowance dated Mar. 7, 2016", 2 pgs.
"U.S. Appl. No. 14/358,065, Response filed Feb. 22, 2016 to Final Office Action dated Nov. 18, 2015", 10 pgs.
"U.S. Appl. No. 14/361,133, Non Final Office Action dated Apr. 15, 2016", 10 pgs.
"U.S. Appl. No. 14/407,783, Non Final Office Action dated Mar. 16, 2016". 10 pgs.
"European Application Serial No. 12849761.7, Response filed Feb. 29, 2016 to Extended European Search Report dated Aug. 7, 2015", 14 pgs.
"European Application Serial No. 13804048.0, Extended European Search Report dated Feb. 9, 2016", 6 pgs.
"U.S. Appl. No. 13/510,825, Response filed Mar. 25, 2015 to Final Office Action dated Dec. 26, 2014", 22 pgs.
"U.S. Appl. No. 13/510,825, Response filed Nov. 19, 2014 to Non Final Office Action dated Jun. 3, 2014", 20 pgs.
"U.S. Appl. No. 14/358,065, Non Final Office Action dated Jul. 31, 2015", 12 pgs.
"U.S. Appl. No. 14/358,065, Response filed Jun. 17, 2015 to Restriction Requirement dated Apr. 20, 2015", 14 pgs.
"U.S. Appl. No. 14/358,065, Restriction Requirement dated Apr. 20, 2015", 7 pgs.
"U.S. Appl. No. 14/407,783, Preliminary Amendment filed Dec. 12, 2014", 13 pgs.
"European Application Serial No. 12849761.7, Extended European Search Report dated Aug. 7, 2015", 7 pgs.

(56) References Cited

OTHER PUBLICATIONS

"European Application Serial No. 12853899.8, Extended European Search Report dated Jun. 29, 2015", 9 pgs.
"European Application Serial No. 12853965.7, Non Final Office Action dated Sep. 9, 2015", 5 pgs.
"International Application Serial No. PCT/US2013/031650, International Preliminary Report on Patentability dated Dec. 24, 2014", 6 pgs.
"Japanese Application Serial No. 2012-541077, Office Action dated Jan. 6, 2015", W/ English Translation, 4 pgs.
"Japanese Application Serial No. 2012-541077, Response filed Apr. 2, 2015 to Office Action dated Jan. 6, 2015", W/ English Translations, 13 pgs.
"Japanese Application Serial No. 2012-541077, Response filed Jun. 17, 2014 to Office Action dated Mar. 18, 2014", with English translation of claims, 10 pgs.
"Japanese Application Serial No. 2014-541415, Office Action dated Dec. 2, 2014", W/ English Translation, 6 pgs.
"Japanese Application Serial No. 2014-541415, Response Office Action dated Dec. 2, 2014", W/ English Claims, 6 pgs.
"Japanese Application Serial No. 2014-543623. Voluntary Amendment filed Jul. 29, 2014", W/ English Claims, 18 Pgs.
"Japanese Application Serial No. 2014-543624, Voluntary Amendment filed Jul. 29, 2014", W/ English Claims, 14 pgs.
"Japanese Application Serial No. 2015-517243, Amendment filed Jan. 30, 2015", W/ English Translation.
"Japanese Application Serial No. 2015-517243, Office Action dated Jun. 16, 2015", W/ English Translation, 9 pgs.
"Japanese Application Serial No. 2015-517243, Response filed Sep. 4, 2015 to Office Action dated Jun. 16, 2015", W/ English Translation, 21 pgs.

* cited by examiner

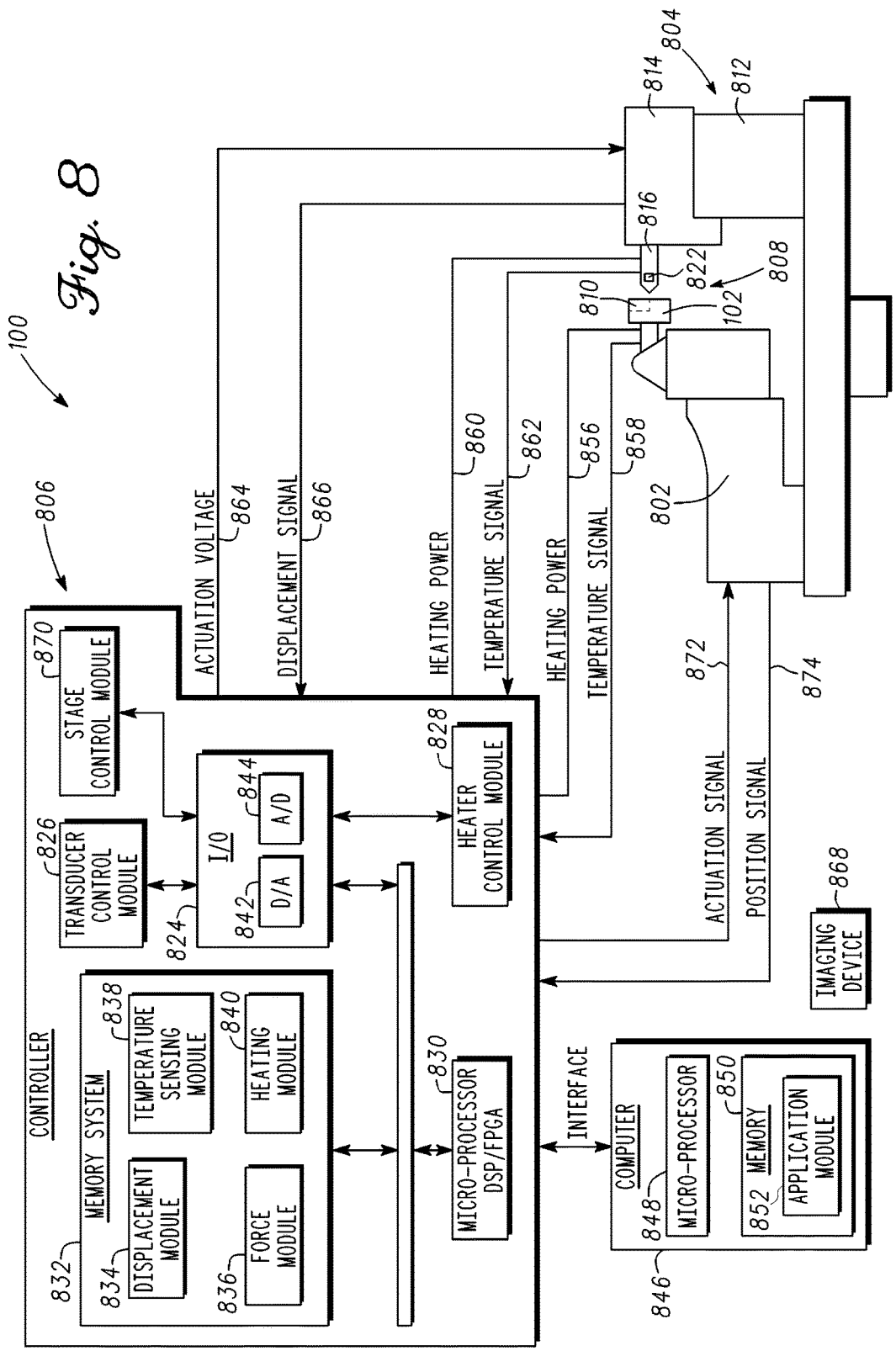

HIGH TEMPERATURE HEATING SYSTEM

CLAIM OF PRIORITY

This patent application is a U.S. National Stage Filing under 35 U.S.C. 371 from International Patent Application Serial No. PCT/US2012/066846, filed Nov. 28, 2012, published on Jun. 6, 2013 as WO 2013/082148 A1, which claims the benefit of priority of U.S. Provisional Patent Application Ser. No. 61/564,188, filed on Nov. 28, 2011 all of which are hereby incorporated by reference herein in its their entirety.

STATEMENT REGARDING FEDERALLY SPONSORED RESEARCH OR DEVELOPMENT

This invention was made with Government support under (FA8650-11-M-5178) awarded by the United States Air Force. The Government has certain rights in this invention.

TECHNICAL FIELD

This document pertains generally, but not by way of limitation, to mechanical testing and heating of samples at scales of microns and smaller.

BACKGROUND

Indentation, scratch, tensile and compression testing at scales of microns or less are methods for quantitatively measuring mechanical properties, such as elastic modulus and hardness, of materials. For instance, probes capable of determining loading forces and displacement are used. In some examples, forces applied in mechanical testing at scales of microns or less are less than 10 N, with a typical displacement range being smaller than 500 µm, and with a noise level typically being better than 10 nm root mean squared (rms). Force and displacement data measured with the probe are used to determine the mechanical properties of the sample and one or more of the elastic or plastic characteristics and the associated material phase changes. In one example, for sample property estimation a micro/nano-indenter is integrated with a characterized indenter tip having a known geometry and known mechanical properties.

Some of the emerging mechanical characterization techniques at scales of microns or less include, but are not limited to, quantitative transmission electron microscopy (TEM) and scanning electron microscopy (SEM) in-situ mechanical testing (as well as optical microscope techniques in some instances). These in-situ mechanical testing techniques enable monitoring of the deformation of a sample in real time while measuring the quantitative mechanical data. Coupling a mechanical testing system configured for testing at scales of microns or less with electron or optical microscopy imaging allows researchers to study structure property correlation and the influence of pre-existing defects on the mechanical response of materials. In addition to imaging, selected-area diffraction can be used to determine sample orientation and loading direction influence on mechanical response. Moreover, with in-situ electron or optical microscopy mechanical testing, the deformation can be viewed in real-time rather than "post-mortem". Performing in-situ mechanical testing at scales of microns or less can provide unambiguous differentiation between the many possible causes of force or displacement transients which may include dislocation bursts, phase transformations, shear banding or fracture onset. Mechanical testing at micron or nano scales with elevated temperature is an important part of material characterization for materials having phase changes or variant mechanical properties as temperature increases. Many materials and devices are designed to perform at temperatures other than room temperature. The thermo-mechanical reliability of advanced materials needs to be fully understood through proper material testing. Due to this reason, it is often preferred to test the mechanical properties of these materials at their operating temperatures. The measured data at the elevated temperature can be used to estimate the performance of the materials in their normal operating environment. For example, understanding the thermo-mechanical response of polymer composites designed for enhanced mechanical properties will result in lighter and stronger materials for aerospace and automobile industries, improving efficiency in the transportation sector and energy savings. Understanding the fundamentals of strengthening mechanisms in ceramic matrix composite materials will help to improve the lifetime usage of these materials in real world applications. To improve the efficiency of turbine powered jet engines, new turbines must run hotter with less cooling. Understanding the mechanical properties at elevated temperature of individual components such as disks, blades and nozzles is critical for the aerospace industry.

OVERVIEW

The present inventors have recognized, among other things, that a problem to be solved can include a sample loaded under tension for testing purposes may fracture along seams or interfaces between the sample, and an underlying sample stage. Adhesives used to couple the sample with the underlying substrate may provide a ceiling of the tensile forces that may be applied to the sample before failure. Elevated tensile forces above this ceiling may be needed for determinant testing of the sample mechanical properties. Additionally, adhesives used with such samples are subject to failure through one or more of the application of tensile forces or heating of the sample or substrate that weakens the adhesive bonds.

In an example, the present subject matter can provide a solution to this problem, such as by a sample gripping and heating assembly that grasps a sample substrate (e.g., a relatively large volume of material compared to a sample head and sample shaft). The sample gripping and heating assembly provides a compressive force to the sample substrate and fixes the substrate in place. A portion of the sample extends from the sample substrate and is available for tensile mechanical testing without an intervening adhesive bond. The gripping surfaces grasp the large volume of the sample substrate and have minimal or no effect on the mechanical properties of the sample portion under examination (e.g., no deformation through the gripping engagement) while leaving the sample portion free for mechanical testing without the adhesive interface.

The sample gripping and heating assembly provides opposed heating elements to simultaneously heat the sample at locations immediately adjacent to the sample. For instance, heating elements are disposed in the gripping surfaces and are configured to heat the sample at the gripping surface interface. Heat transfer is realized at the interface without conducting the heat transfer from more remote locations in the sample gripping and heating assembly. Further, heat transfer to remote portions of the sample gripping and heating assembly is substantially throttled through a combination of the shape of the sample gripping and heating assembly and the material selection for the heating grips and grip bases.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 8 is a block diagram of one example of a nano-mechanical test system.

DETAILED DESCRIPTION

According to embodiments described herein, a system and method are provided for mechanically testing samples at the nano and micro scales (i.e., scales of microns or less), including, but not limited to, nanostructures, thin films and the like. Such testing is performed, in one example, to determine the mechanical properties of the materials composing the subjects. According to one embodiment, as will be described in greater detail herein, the testing assembly described herein includes a heating system including a sample gripping and heating assembly having heating and sensing elements positioned adjacent to a sample. The sample gripping and heating assembly grasps a sample substrate (e.g., a relatively large volume of material compared to a sample head and sample shaft). The sample gripping and heating assembly provides a compressive force to the sample substrate and fixes the substrate in place. A portion of the sample optionally extends from the sample substrate and is available for tensile mechanical testing without an intervening adhesive bond. The gripping surfaces grasp the large volume of the sample substrate and have minimal or no effect on the mechanical properties of the sample portion under examination (e.g., no deformation through the gripping engagement) while leaving the sample portion free for mechanical testing without an adhesive interface.

The sample gripping and heating assembly provides opposed heating elements to simultaneously heat the sample at locations immediately adjacent to the sample. For instance, heating elements are disposed in the gripping surfaces and are configured to heat the sample at the gripping surface interface. Heat transfer is realized at the interface without conducting the heat transfer from more remote locations in the sample gripping and heating assembly. Further, heat transfer to remote portions of the sample gripping and heating assembly is substantially throttled through a combination of the shape of the sample gripping and heating assembly and the material selection for the heating grips and grip bases.

Figure 1:
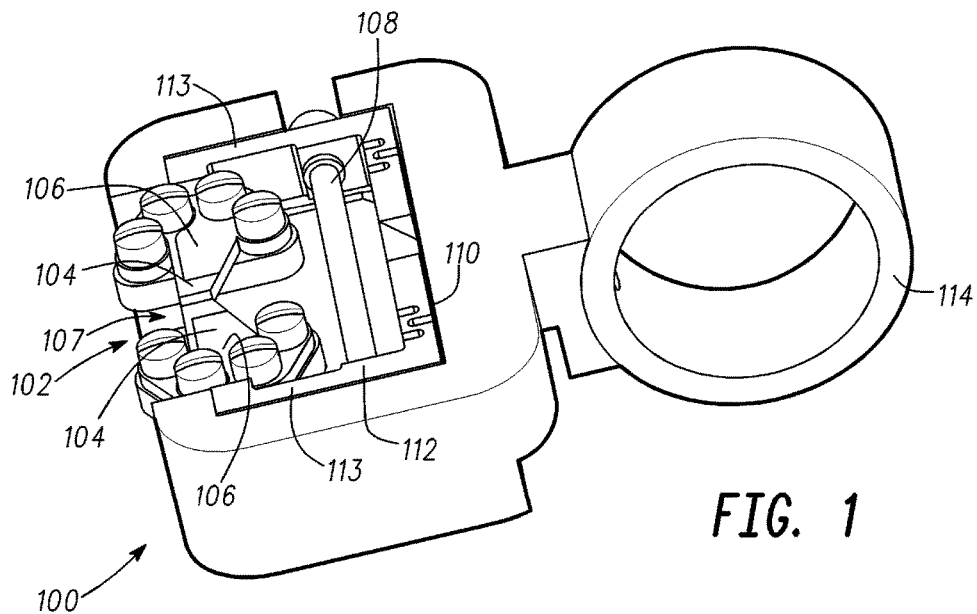
FIG. 1 is a perspective view of one example of a high temperature sample testing system.

FIG. 1 shows one example of a high-temperature sample testing system 100. As shown the high-temperature sample testing system 100 includes a sample gripping and heating assembly 102 including, for instance, two or more heating grips 104 (e.g., jaws) positioned on either side of an assembly housing 112 of the sample gripping and heating assembly 102. As further shown, the sample gripping and heating assembly 102 in one example includes a grip base 106 for each of the heated grips in 104. For instance, the heating grips 104 extend from or are a part of the grip bases 106. In another example, the sample gripping and heating assembly 102 includes a grip actuator 108 extending between clamp arms 113 (e.g., grip arms) at an assembly housing 112. The grip actuator 108 is sized and shaped to provide clamping force to each of the clamp arms 113 through operation of the grip actuator 108 to gradually move the heating grips 104 inwardly toward one another to grip and thereby clamp a sample positioned between the heating grips 104.

As shown in FIG. 1, the assembly housing 112 of the sample gripping and heating assembly 102 is positioned within an assembly socket 110 forming a fixture for the assembly housing 112. In one example, the assembly socket 110 (e.g., a gripping assembly coupling feature) is sized and shaped for coupling with the stage interface 114 (e.g., a stage coupling feature). Optionally, the assembly socket 110 and the stage interface 114 form a stage adaptor configured for coupling with a stage (e.g., the stage 802 shown herein). For instance, in one example the stage interface 114 includes a spindle ring of a tilting or rotating stage of a multiple degree of freedom stage including one or more of rotating, tilting and one or more linearly positionable stages sized and shaped to move the sample gripping and heating assembly 102 including a sample gripped between the heating grips 104 into any number of discreet orientations for interaction with one or more instruments of a mechanical testing assembly such as the mechanical testing assembly described herein. Optionally, the sample gripping and heating assembly 102 coupled with a stage adaptor is configured for use with any instrument having a moving or static stage that would benefit from heating of a sample during testing of the sample including, but not limited to, optical microscopes, electron microscopes and other instruments. In still another example, the sample gripping and heating assembly 102 is coupled directly with an instrument (e.g., an objective stage) without the intervening adaptor.

Referring again to FIG. 1, in operation the heating grips 104 coupled with the grip bases 106 are positioned on either side of a sample gap 107. Operation of the grip actuator 108, for instance, a threaded screw received in each of the clamp arms 113 moves the clamp arms 113 (e.g., grip arms) inwardly and thereby correspondingly moves the heating grips 104 into a gradually closer orientation relative to one another. The gradual movement of the heating grips 104 grasps and anchors a sample positioned there between for eventual interaction with an instrument that extends between the grip bases 106 to interact with the sample positioned between the heating grips 104. In one example, the grip actuator 108 includes a screw having opposing threads sized and shaped for engagement with corresponding threading in orifices of each of the clamp arms 113. In another example, the grip actuator 108 includes a compression fitting sized and shaped to provide clamping, for instance through one or more of spring actuation, a mechanical torqueing mechanism that gradually clamps the clamp arms 113 (e.g., grip arms) together, and the like. In another example, the grip actuator 108 includes an actuator such as a piezo actuator configured to engage one or both of the clamp arms 113 and thereby push or pull the clamp arms 113 toward one another to thereby move the heating grips 104 into closer engagement for eventual anchoring of a sample therebetween.

Figure 2:
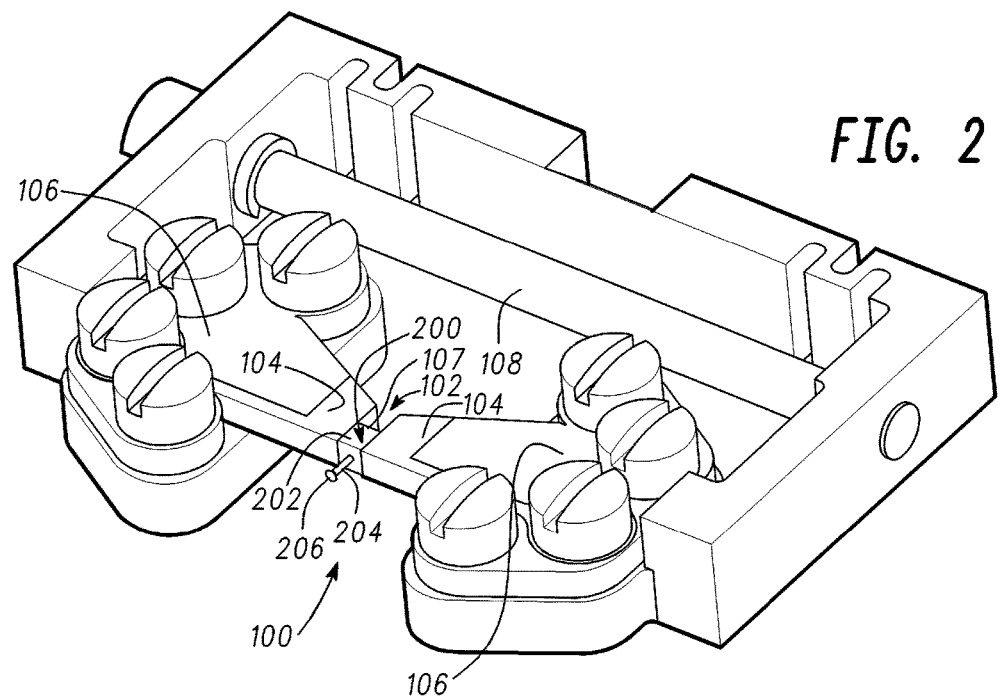
FIG. 2 is a detailed perspective view of one example of a sample gripping and heating assembly.

FIG. 2 shows a detailed view of the high-temperature sample testing system 100 previously shown in FIG. 1. As shown in FIG. 2, the heating grips 104 are shown positioned on either side of the sample gap 107. A sample 200 is shown clamped between the heating grips 104. In one example, the sample 200 includes a sample substrate 202 for instance a block, slug, base, and the like of a material sized and shaped for gripping by the heating grips 104. In one example, the sample substrate 202 is constructed with the same material as the sample shaft 204 and the sample head 206. For instance, in one example the sample 200 is a machined sample formed by focused ion beam (FIB) lithography, ion milling, masking, etching, and the like to form the sample shaft 204 and the sample head 206. The sample shaft 204 in one example is formed as an integral portion of the sample substrate 202. For instance, as described above the sample 200 is formed from a unitary piece of material with the sample shaft 204 being of interest for testing.

As further shown in FIG. 2, the sample shaft 204 includes at an opposed end to the sample substrate 202 a sample head 206. The sample head 206 in one example is a flange, rounded nubbin, or other feature having a larger area, circumference or diameter from the sample shaft 204. The sample head 206 allows for easy grasping of the sample head 206, for instance, for tensioning of the sample shaft 204 during a mechanical testing procedure (tensile testing, creep testing and the like). In one example, a mechanical testing instrument is engaged around or coupled with the sample head 206 to provide tensile stress to the sample shaft 204. In one example, the sample shaft 204 is examined for its tensile modulus and the like during mechanical testing by tensile loading of the sample shaft 204 between the sample head 206 and the sample substrate 202.

As previously described herein, in one example the sample 200 is formed from a unitary piece of material that is of interest for testing purposes. By forming the sample 200 with a unitary piece of material, the sample shaft 204 is not in this example coupled with the sample substrate 202 (or the high temperature sample testing system 100) with an adhesive. Instead, the sample shaft 204 is integral to the sample substrate 202 thereby avoiding the interposition of adhesives therebetween. In another example, the sample shaft 204 is a unitary component with the sample head 206 thereby avoiding the provision of adhesives therebetween as well. The exclusion of adhesives from the sample 200 thereby allows for the tensile loading of the sample 200 without the provision of an adhesive between one or more of the sample shaft 204 and the sample head 206 as well as the sample shaft 204 and the sample substrate 202, an otherwise limiting mechanical feature that could otherwise provide an upper non-sample based limit to the tensile loading of the sample shaft 204. Stated another way, stress risers at the adhesive interface between one or more of the sample shaft and the sample substrate 204, 202 are avoided by the integral formation and gripping of the sample 200. Tensile loading of the sample shaft 204 thereby does not cause failure at a discontinuous interface between the sample shaft 204 and the sample substrate 202, for instance, where adhesives would be used to couple the two components together. Further the sample gripping and heating assembly 102 grasps the sample mechanically and further avoids the need for adhesives and the like to couple the sample 200 with the high temperature sample testing system.

Referring again to FIGS. 1 and 2, in one example the assembly socket 110 and the assembly housing 112 are sized and shaped to include electrical pass-through such as leads and contacts for the same extending from the heating grips 104 and the heating elements (e.g., for heating and temperature sensing) disposed therein. For instance, the assembly socket 110 and the assembly housing 112 include electrical leads therethrough for the operation of the heating elements as well as for coupling of electron discharges as described herein. In one example, the electrical leads are passed through the stage interface 114 for coupling with corresponding features in the stage. In another example, where the stage includes a multiple degree of freedom stage the multiple degree of freedom stage includes electrical leads, wires, and the like sized and shaped to electrically couple with the leads for the heating and temperature sensing elements as well as the electron discharges for each of the heating grips 104.

In one example, the high-temperature sample testing system 100, for instance, the heating grips 104 is constructed with zirconia, fused quartz, or other materials having a high mechanical strength, elastic modulus, high melting point and the like.

The grip bases 106, the assembly socket 110 and the assembly housing 112 are constructed with one or more of alumina, aluminum or other materials having high mechanical strength and high thermal conductivity and the like. Additionally, the materials used in the high-temperature sample testing system 100 include in another example materials having high elastic moduli configured to maintain the high-temperature sample testing system 100 in a static orientation during compression and tension, for instance during testing of a sample disposed within the sample gap 107 between the heating grips 104. Stated another way, the high-temperature sample testing system 100 provides a rigid supporting base to the sample position between the heating grips 104 whether at ambient or elevated temperatures such as 1,100 to 1,200 degrees Celsius and the like.

Figure 3A:
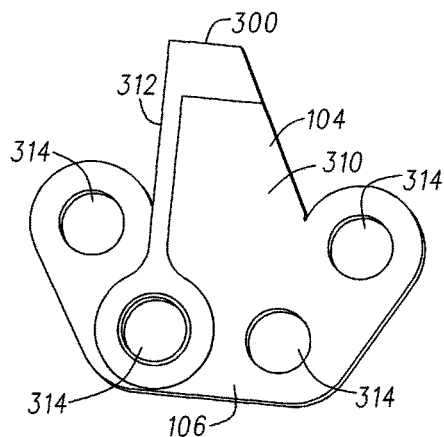
FIG. 3A is a perspective view of a front view of one example of a heating grip.
Figure 3B:
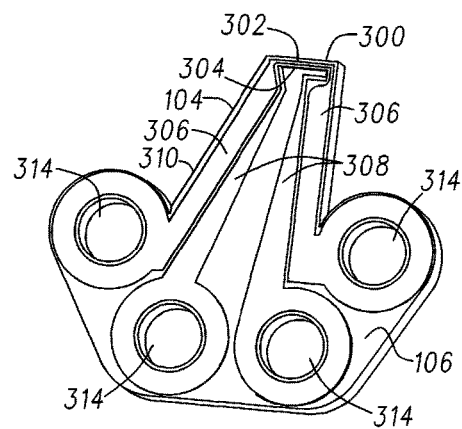
FIG. 3B is a perspective view of a back view of the heating grip shown in FIG. 3A.

FIGS. 3A and 3B show respective front and back views of each of the heating grips 104 previously shown in FIG. 1. In one example, the heating grips 104 include a gripping surface 300, such as a jaw surface sized and shaped to engage with the sample positioned within the sample gap 107 previously shown in FIG. 1. The gripping surface 300 of the heating grips 104 is positioned remotely relative to a grip base 106. In one example, a base neck 310 extends from the grip base 106 to the gripping surface 300. For instance, the base neck 310 provides a tapering or narrow feature extending from the grip base 106 to the gripping surface 300. The narrowing of the heating grip 104 between the grip base 106 and the gripping surface 300 substantially throttles heat transfer from the gripping surface 300 for instance at a heating element 302 into the remainder of the grip base 106 and thereby substantially limits the elevation of temperature within the grip base 106 and correspondingly minimizes the expansion of the grip base 106 during heating of the sample within the sample gap 107 (see FIG. 1).

Referring to FIG. 3B, the back side of the heating grip 104 is shown. As shown, the heating grip 104 includes a heating element 302 and a temperature sensing element 304 positioned adjacent to the gripping surface 300. As further shown, heating leads 306 electrically couple the heating element 302 with corresponding end portions of the heating leads 306 at two of the fastener orifices 314. Similarly, sensing leads 308 extend from the temperature sensing element 304 to the fastener orifices 314 for eventual coupling with corresponding electrical pass-through within the assembling housing 112 and the assembly socket 110, for instance, through fasteners such as brass screws as shown in FIG. 1. As shown, the heating and sensing elements 302, 304 are positioned remotely relative to the grip base 106 to localize the heating of the gripping surface 300 to just the volume of the heating grips 104 adjacent to the gripping surface 300. In one example the heating and sensing elements 302, 304 as well as the corresponding leads 306, 308 are constructed with but not limited to silicon carbide elements and leads extending across the heating grips 104 as shown in FIG. 3B.

Referring now to the front of the heating grip 104 shown in FIG. 3A, an electron discharge trace 312 is shown extending from the gripping surface 300 to one of the fastener orifices 314. As shown, the electron discharge trace 312 in one example is constructed with a conductive silicon carbide lead and element combination extending from the gripping surface 300 to the fastener orifice 314. The electron discharge traces 312 of each of the heating grips 104 provide a ready means to eliminate charging effects when used in a scanning electron microscope. The electron discharges traces 312 pass out of the sample and through the high-temperature sample testing system 100. The electron discharge trace 312 is optionally connected to either an electron microscope ground or a testing system ground associated with the stage coupled with the high-temperature sample testing system 100 (such as an instrument assembly, stage or multiple degree of freedom sample stage as described herein).

As further shown in FIGS. 3A and 3B, the gripping surfaces 300 are positioned at the ends of the base necks 310, for instance, remotely relative to the grip bases 106. In one example, the gripping surfaces 300 provide a substantially flat surface sized and shaped for mechanical engagement with a sample such as the sample 200 positioned between two or more heating grips 104. In one example, the gripping surfaces 300 are planar and provide for surface-to-surface contact between the sample 200 and the gripping surfaces 300. The conduction of heat, for instance, from the heating element 302 is thereby readily achieved from the gripping surfaces 300 to the sample 200. In another example, the gripping surface 300 has a knurled, corrugated or roughened surface sized and shaped to engage with the sample 200 and provide enhanced gripping of the sample 200 therebetween. In such an example, the clamping action of the heating grips 104, for instance, through operation of the grip actuator 108 provides a ready conductive coupling between the sample 200 and the gripping surfaces 300. By positioning the sample 200 in an immediately adjacent position relative to the gripping surfaces 300 as well as the adjacent heating element 302 and temperature sensing elements 304, heat is readily conducted to the sample 200 as well as the sample shaft 204 and the sample head 206 during mechanical testing of the sample 200.

Additionally, with control of heating of the heating elements 302 for each of the opposed heating grips 104, a heating gradient between the opposed heating grips 104 is substantially prevented. For instance, each of the heating elements 302 are heated to substantially identical temperatures (e.g., through monitoring of the sensing elements 304) thereby ensuring heat conducted to the sample 200 is done so without a gradient between opposed heating grips 104. Stated another way, heat transfer from one heating grip, through the sample 200 to an opposed heating grip 104 is thereby substantially avoided. Instead, with the heating grips 104 including their heating elements 302 heated to the same degree, the sample 200 is elevated to a temperature without transferring heat to one of the other opposed heating grips 104. This arrangement of the heating elements 302 of the opposed heating grips 104 substantially ensures the sample 200 is elevated to a temperature as desired and maintained at that desired temperature until such time that heating is no longer desired and heating during the testing procedure is concluded.

Figure 4A:
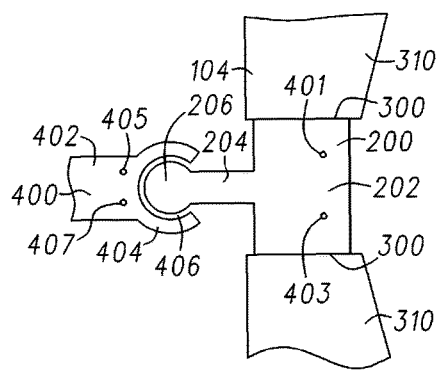
FIG. 4A is a top view of the sample gripping and heating assembly, coupled with a sample, and a sample portion is engaged with a mechanical testing instrument.

Referring now to FIG. 4A, one example of a gripping probe 400 is shown in an engaged orientation with the sample 200 previously shown in FIG. 2. As shown, the sample 200 is coupled between the heating grips 104 of the grip bases 106 of the high-temperature sample testing system 100 previously shown in FIG. 1. As described above, the heating grips 104 include gripping surfaces 300 sized and shaped to engage with the sample 200 and clamp the sample therebetween for testing with the instruments such as the gripping probe 400. As further described previously, the sample 200 includes the sample substrate 202, sample shaft 204 and a sample head 206.

Referring now to FIG. 4A, the gripping probe 400 (e.g., a mechanical testing instrument) is shown with a probe shaft 402 and a gripping tip 404. In the example shown in FIG. 4A, the gripping tip 404 includes a corresponding geometry such as a semi-circular geometry configured to extend around a portion of the sample head 206. The corresponding shape of the gripping tip 404 to the sample head 206 provides a coupling relationship between the sample 200 and the gripping probe 400. In one example, the gripping tip 404 is sized and shaped to grip around the sample head 206 and ensure that tensile forces applied to the griping probe 400 are transmitted to the sample shaft 204 for testing of the sample 200. For instance, the gripping tip 404 includes a tip socket 406 having a corresponding shape to the sample head 206. Reception of the sample head 206 therein allows for a clamping or grasping engagement of the sample head 206 to ensure tensile forces applied to the gripping probe 400 are transmitted to the sample 200, for instance, the sample shaft 204. Optionally, the gripping tip 404 applies compressive force to the sample 200.

In another example, the gripping tip 404 includes one or more features sized and shaped to engage with the sample 200 and thereby apply one or more of tensile or compressive forces to the sample 200. For instance, the gripping tip 404 includes a clamp, a hook, a mechanical feature and the like sized and shaped to engage the corresponding features of the sample 200, for instance, at the sample head 206 to ensure fixed engagement of the gripping probe 400 with the sample 200 and corresponding transmission of tensile or compressive loads to the sample shaft 204 throughout a testing procedure without losing the grasp of the sample 200 during that testing procedure.

As further shown in FIG. 4A and previously described herein, the gripping surfaces 300 are sized and shaped to provide surface-to-surface contact with corresponding surfaces of the sample 200. The surface-to-surface contact between the sample 200 and the gripping surfaces 300 allows for the ready conduction of heat from the gripping surfaces, for instance, the heating grips 104 having the heating elements 302 position therein to the sample 200 including the sample shaft 204 and the sample head 206. Additionally, the positioning of the temperature sensing elements 304 as shown in FIG. 3B immediately adjacent to the sample 200 allows for the ready measurement of temperature of the sample 200 as well as the heating grips 104 during operation of the high-temperature sample testing system 100.

Additionally, the high-temperature sample testing system 100 as described herein, including for instance one or more of probes (for instance the gripping probe 400 or any of the other probes provided herein) and the heating grips 104 (including any of the grip configurations herein) is also configured for use with any mechanical, electro-mechanical or electrical based testing assembly or instrument that would benefit from one or more of a heated sample or probe. For instance, for electrical, electro-mechanical, thermo-electrical, or thermo-electro-mechanical testing (e.g., electrical based testing), a voltage or current is applied through the probe and the sample, and the resistance or capacitance change of the sample or probe-sample contact area is measured, for instance with an electrical characteristic module of the controller 806 (e.g., within the memory system 832). In another example, electrical, electro-mechanical, thermo-electrical, or thermo-electro-mechanical testing is conducted with the sample electrically connected (e.g., by way of voltage or current application) to measure the resistance or capacitance change while the sample is heated, mechanically stressed or both. With this measurement scheme only the sample is connected to the source of electricity and only the sample is measured. The probe 400 may optionally provide mechanical pressure (stress, force or the like) to the sample but is not used to measure the electrical properties of the sample. In another example, the probe 400 also conducts mechanical testing during the electrical based testing.

As described herein and shown in FIG. 4A, the electrical connections, such as contacts for providing electricity to one or more of the probe 400, the heating grips 104 or the sample directly, are shown in exemplary FIG. 4A (all of the probe and heating grip configurations herein are readily modified to include these contacts (e.g., electrodes)). For instance, as shown in FIG. 4A, a voltage application contact 401 and a current application contact 403 are adjacently provided on the sample 200. In this configuration, the heating grips 104 optionally electrically isolate the sample 200 from the remainder of the sample gripping and heating assembly 102 (and any stage or instrument coupled with the assembly). Similarly, the probe 400 includes a corresponding voltage application contact 405 and a current application contact 407. Leads corresponding to the contacts 405, 407, 401, 403 extend proximally along a shaft of the probe 400 and optionally through the sample gripping and heating assembly 102 to power the contacts. The contacts 401, 403, 405, 407 are used for the testing methods described herein including, but not limited to, 2-point probe measurement, 4-point probe measurement and the like. Optionally, the voltage application contact 401 and the current application contact 403 are coupled with the heating grips 104, and leads are run from the heating grips 104 (through the sample gripping and heating assembly 102) to apply one or more of voltage or current across the heating grips to the sample 200.

With the probe 400, the portion that contacts a sample may be electrically conductive (e.g. tungsten, conductive diamond and the like). With electrical insulation between the gripping tip 404 and the remainder of the probe (e.g., the probe 400), at least a portion of the tip 404 is electrically isolated from the rest of the probe 400. Leads are attached to one or more of the voltage application contact 405 or the current application contact 407 to accordingly electrically test through the probe tip 404. Optionally, as described above, the sample is electrically isolated from the probe tip 404 and the heating grips 104, and electrical leads are coupled directly with the sample for electrical based testing of the sample (with contacts 401, 403). In another option, the sample 200 is electrically isolated from the probe tip 404 and the heat grips 104 apply one or more of current or voltage to the sample 200 through the contacts 401, 403 provided on the heat grips 104. The system (e.g., the system 100) is accordingly used for electrical measurements in conjunction with (or separately from) heating and mechanical testing. For example, the contacts on the probe 405, 407 along with the contacts attached to the sample (e.g., 401, 403) are part of a 4-point electrical measurement system that monitors and measures electrical resistivity changes during tensile or compressive deformation of the sample. In another example, additional leads and contacts are provided to the sample (200 or any of the other samples provided herein), the heating grips 104, and the probe 400 (or any of the other probe examples provided herein) for more extensive electrical measurements.

Figure 4B:
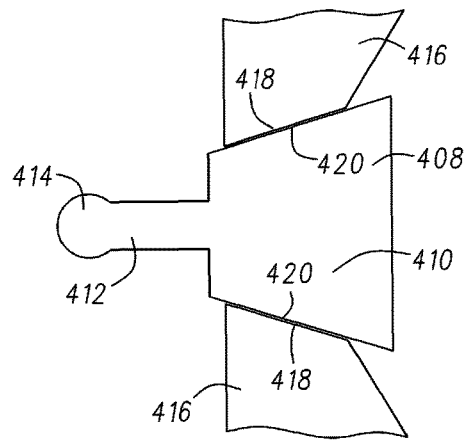
FIG. 4B is a top view of another example of a sample gripping and heating assembly coupled with a graduated sample.

Referring now to FIG. 4B, another example of a high-temperature sample testing system is provided including tapered heating grips 416. As shown in FIG. 4B a graduated sample 408 is positioned between the tapered heating grips 416. The graduated sample 408 includes a sample substrate 410, a sample shaft 412 and a sample head 414. In at least some regards the graduated sample 408 is similar to the sample 200 previously described herein. For instance, the sample head 414 is configured to provide corresponding coupling with an instrument such as the gripping probe 400 previously shown in FIG. 4A. Referring again to FIG. 4B, the tapered heating grips 416 provide a tapered gripping surface 418 on each of the heating grips 416. The tapered gripping surface 418 is sized and shaped to correspondingly engage with tapered substrate surfaces 420 on both sides of the sample substrate 410. The engagement of the tapered gripping surfaces 418 with the tapered substrate surfaces 420 provides a locking engagement for the graduated sample 408 when experiencing tensile loads applied to the sample shaft 412 for instance through engagement of the sample head 414 by the gripping probe 400. Stated another way the compressive forces applied by the tapered heating grips 416, for instance, by operation of a grip actuator such as the grip actuator 108 shown in FIG. 1 are supplemented by the mechanical engagement of the tapered surfaces 418, 420 of the tapered heating grips 416 and the sample substrate 410. The combination of the mechanical engagement between the tapered surfaces as well as the compressive forces applied by the opposed tapered heating grips 416 provides an affirmative coupling to the graduated sample 408 with the high-temperature sample testing system including the tapered heating grips 416 and ensures that the graduated sample 408 is reliably retained in the desired position throughout the testing scheme. Optionally, an opposed tapering surface or flange is provided (e.g., to the right of the tapered gripping surfaces 418 in FIG. 4B) for the heating grips 416 to further fix the graduated sample 408 in place against compressive forces.

Figure 4C:
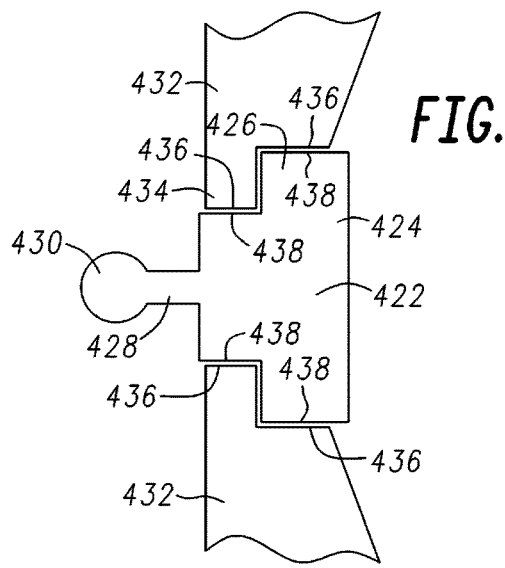
FIG. 4C is a top view of yet another example of a sample gripping and heating assembly coupled with a stepped sample.

FIG. 4C shows yet another example of a high-temperature sample testing system including stepped heating grips 432. As further shown in FIG. 4C, a corresponding stepped sample 422 is interposed between the stepped heating grips 432. In a similar manner to the previously described examples, the stepped sample 422 includes a sample substrate 424, a sample shaft 428 and a sample head 430. As shown in FIG. 4C, the sample substrate 424 in this example includes a substrate flange 426 providing for a stepped engagement with the corresponding stepped heating grips 432.

As shown, the stepped heating grips 432 include a grip flange 434 on each of the stepped gripping surfaces 436. The grip flanges 434 are configured for corresponding engagement along or within the substrate flange 426 of the stepped sample 422. The engagement of the grip flange 434 with the substrate flange 426 provides an affirmative mechanical engagement (e.g., an interference fit) between the stepped sample 422 and the stepped heating grips 432. The mechanical interface between the stepped heating grips 432 and the stepped sample 422 (at the grip flange 434 and the substrate flange 426) is used in combination with mechanical compression, for instance, at the interface between the stepped gripping surface 436 of the stepped heating grips 432 and the stepped substrate surfaces 438 of the stepped sample 422. Stated another way, the clamping engagement of the stepped gripping and substrate surfaces 436, 438 is combined with the mechanical engagement of the grip flange 434 with the substrate flange 426 to provide a reliable fixed mechanical coupling of the stepped sample 422 to the stepped heating grips 432 (and correspondingly a high-temperature sample testing system incorporating the same) throughout tensile testing of the stepped sample 422. In another example, the engagement, whether the tapered surfaces shown in FIG. 4B or the stepped surfaces shown in FIG. 4C, is equally applicable to compressive loading of the corresponding samples 408, 422. For instance, in compressive loading the clamping engagement of the tapered heating grips 416 and the stepped heating grips 432 with the corresponding sample ensures the graduated sample 408 and the stepped sample 422 are reliably engaged between the grips to substantially prevent movement of the sample during compressive loading (e.g., indenting, scratching, and the like).

Referring again to FIG. 1, the high-temperature sample testing system 100, for instance, the assembly housing 112 is shown positioned within an assembly socket 110 of a stage interface 114. In one example, the assembly housing 112 is a modular component sized and shaped for reception within the assembly socket 110 after mechanical setup of the sample gripping and heating assembly 102. Referring to FIG. 2, in one example the sample 200 is positioned between the heating grips 104, for instance, with an intermediate clamping or positioning mechanism or instrument. The grip actuator 108 is operated to gradually close the clamp arms 113 relative to one another. The gradual clamping of the clamp arms 113 correspondingly moves the heating grips 104 into closer engagement with one another. The heating grips 104 with continued movement of the grip actuator 108 engage with the sample 200 and mechanically hold and fix the sample 200 in the position shown in FIG. 2. The grip actuator 108 is further operated (to reliably clamp the sample in place) to ensure fixed coupling of the sample 200 between the heating grips 104 and to ensure reliable conduction of heat from the heating elements 302 to the sample 200. Operation of the grip actuator 108 in one example automatically locks the clamp arms 113 in a clamping configuration with the heating grips 104 engaged with sample 200 as described herein.

The assembly housing 112, after configuring into the clamping configuration shown in FIG. 1, is thereafter positioned within the assembly socket 110 of the stage interface 114. In one example, the assembly of the assembly housing 112 is performed outside of a mechanical testing system, for instance, a scanning electron microscope, and the assembly housing 112 is thereafter positioned within the assembly socket 110 as a modular unit. In one example, one or more of the clamp arms 113 or any portion of the assembly housing 112 includes corresponding electrical contacts to ensure that electrical coupling of one or more of the heating elements 302, temperature sensing elements 304 and electron discharges 312 of the heating grips 104 is provided to the stage interface 114 and corresponding wiring of the mechanical testing system (e.g., of the microscope of a multiple degree of freedom stage of a mechanical testing instrument, and the like) with installation of the assembly housing 112 within the socket 110. The assembly housing 112 including the heating grips 104 is thereby able to provide a readily assembled and compact fixture sized and shaped for modular position within a corresponding socket such as the assembly socket 110 of the stage interface 114. Time consuming and labor intensive positioning and adhering of a sample, for instance, to a stage substrate is thereby avoided. Instead, a previously machined or formed sample is gripped or clamped between the heating grips 104 and thereafter readily positioned as a unitary assembly (with the assembly housing 112) within the assembly socket 110 for ready testing by a mechanical testing instrument including the high-temperature sample testing system 100.

Additionally the modular assembly of the assembly housing 112 provides a ready means to easily heat the sample 200 positioned between the heating grips 104. Because each of the heating grips 104 are separately heated to identical temperatures, the heat transfer gradient across the sample 200 is substantially minimal or 0 thereby ensuring heat generated from the opposed heating grips 104 is fully transferred to the sample 200 without corresponding transmission to the opposed heating grips 104. Stated another way, heat transferred to the sample 200 stops at the sample and does not cross the sample to an opposed heating grip thereby avoiding an uncontrolled temperature drop in the sample 200.

In another example and as previously described herein, the high-temperature sample testing system 100 is coupled with a multiple degree of freedom stage such as a stage having one or more of rotational, tilting and linear positioning of the sample relative to one or more mechanical testing instruments. For instance, the high-temperature sample testing system 100 is coupled with a multiple degree of freedom sample stage with a stage interface, such as the stage interface 114 shown in FIG. 1. The rotational, tilting and linear positioning of the sample 200, for instance, within the high-temperature sample testing system 100 allows for the ready alignment of one or more features of the sample 200 (e.g., multiple sample portions at multiple locations on the sample) with the mechanical testing instrument. In another example, the mechanical testing instrument such as the gripping probe 400 is coupled with its own staging system, for instance, linear actuators. The linear actuators of the gripping probe 400 cooperate with the one or more linear, tilting and rotational actuators of the multiple degree of freedom stage to provide even greater flexibility for the ready positioning and coupling of one or more of the sample features such as the sample head 206 with the corresponding gripping tip 404 of the gripping probe 400 (or any other mechanical testing instrument of the system).

Figure 5B:
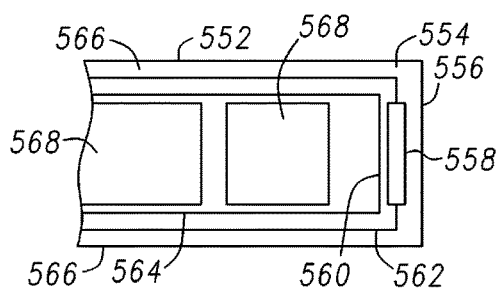
FIG. 5B is a top view of another example of a mechanical testing instrument configured for heating.
Figure 5A:
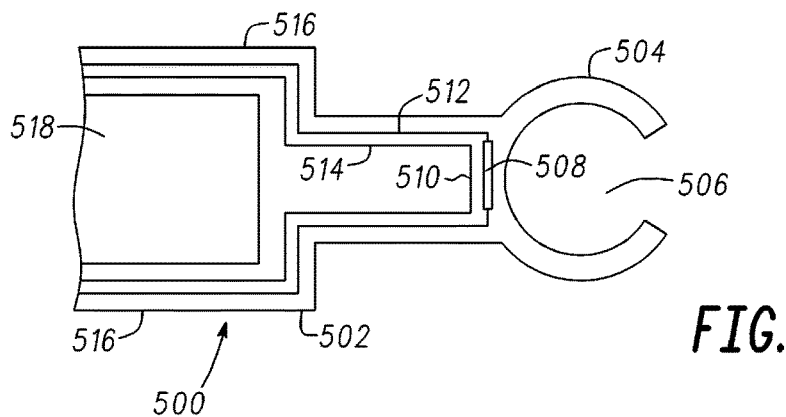
FIG. 5A is a top view of one example of a mechanical testing instrument configured for heating.

FIG. 5A shows one example of a mechanical testing instrument, for instance, a mechanical testing instrument or gripping probe used for tensile testing of a sample coupled with the sample gripping and heating assembly 102 shown in FIG. 1. In one example, the mechanical testing instrument 500 includes a probe shaft 502 and a gripping tip 504. In at least some regards the mechanical testing instrument 500 is similar to the gripping probe 400 shown in FIG. 4A. For instance, the gripping tip 504 includes a tip socket 506 sized and shaped to receive a sample head, such as the sample head 206 shown in FIG. 2. The gripping tip 504 is thereby able to engage with the sample head 206 and tension the sample 200, for instance the sample shaft 204, to test and examine the sample under tension (e.g., for tensile modulus determinations).

As shown in FIG. 5A, in one example, the mechanical testing instrument 500 includes a heating element 508 and a sensing element 510. In one example, the heating and sensing elements 508, 510 are resistive elements configured for heating the gripping tip 504 and sensing the temperature of the gripping tip 504 (and a sample engaged with the gripping tip). Heating leads 512 extend from the heating element 508 proximally toward an opposed end of the probe shaft 502, for instance, to couple the heating element 508 with control and operation electronics. Similarly, sensing leads 514 for the sensing element 510 extend proximally for coupling with control and sensing electronics configured to measure the temperature at the gripping tip 504.

Referring again to FIG. 5A, in one example, the mechanical testing instrument 500 includes the gripping tip 504 positioned at an end or distally relative to a proximal portion of the probe shaft 502 by support columns 516. In one example, the probe shaft 502 including the all or part of the mechanical testing instrument 500 are constructed with materials having low coefficients of thermal expansion and low thermal conductivities (e.g., fused quartz, sapphire and the like). The support columns 516 shown in FIG. 5A provide another heat throttling feature in combination with the materials used for the probe shaft 512. For instance, the support columns 516 have a smaller cross sectional area transverse to a longitudinal axis of the probe shaft 502 compared to the gripping tip 504. The support columns 516 thereby throttle heat transfer from the heating element 508 proximally into the remainder of the probe shaft 502. Stated another way, the combination of the support columns 516 as well as the materials of the probe shaft 502 cooperate to substantially throttle heat transfer out of the gripping tip 504. Instead, heat is generated and localized within the gripping tip 504.

In one example, the gripping tip 504 is elevated to temperatures substantially identical to the temperature of the gripping surfaces 300 shown in FIGS. 3A and 3B engaged with the sample 200 positioned therebetween. By elevating the temperature of the gripping tip 504 to the gripping surfaces 300 the sample 200 is tested at a specified temperature without heat transfer between the mechanical testing instrument 500 and the sample gripping and heating assembly 102 (see FIG. 1). By substantially eliminating any heat transfer between the mechanical testing instrument 500 and the sample gripping and heating assembly 102 the sample 200 coupled therebetween and tested with the mechanical testing instrument 500 is reliably elevated to the testing temperature and thereafter tested at the specified testing temperature without heat transfer and corresponding uncontrolled lowering of the temperature of the sample 200 during the testing procedure.

Referring again to FIG. 5A, one or more voids, windows or gaps 518 are shown positioned between the support columns 516. In one example, the windows, gaps or voids 518 provide an additional heat transfer throttling feature to the probe shaft 502. For instance, the voids 518 provide a gap to substantially retard heat transfer along the probe shaft 502 for instance, to the proximal portion of the probe shaft 502 coupled with a mechanical testing assembly. In one example, where the mechanical testing instrument 500 and the sample gripping and heating assembly 102 are used within a microscope environment including a vacuum chamber the void 518—emptied of atmosphere by virtue of the vacuum—substantially prevents the convective heat transfer from the gripping tip 504 proximal along the probe shaft 502. Additionally, in a vacuum or non-vacuum environment the void 518 substantially retards radiative heat transfer across the void 518, for instance to the proximal portions of the probe shaft 512. By throttling or eliminating the heat transfer from the gripping tip 504 to the proximal portions of the probe shaft 502 undesirable expansion and thermomechanical noise of the mechanical testing instrument 500 are substantially avoided or minimized. For instance, heating of the mechanical testing instrument 500 is localized to the gripping tip 504 while the remainder of the probe shaft 502 including the proximal larger volume portions of the probe shaft 512 coupled with the remainder of the mechanical testing assembly are substantially isolated from heat transfer from the gripping tip 504. Expansion and thermomechanical noise of these larger portions of the mechanical testing instrument 500 are thereby eliminated or substantially minimized.

FIG. 5B shows another example of a mechanical testing instrument 550. In this example, the mechanical testing instrument 550 is a compressive testing instrument including a probe shaft 552 and a planar punch tip 554. As shown in FIG. 5B, the planar punch tip 554 includes a planar punch surface 556 sized and shaped for engagement with the sample, for instance in surface to surface contact between the planar punch surface 556 and a corresponding planar surface of the sample. In one example, the planar punch surface 556 is engaged with a sample having a columnar configuration. The engagement of the planar punch surface 556 compresses the column sample and facilitates the observation of mechanical properties of the columnar sample, such as the compressive modulus, creep characteristics and the like through measurement of forces and displacement of the mechanical testing instrument 550.

In another example, the mechanical testing instrument 550 shown in FIG. 5B includes one or more support columns 566 with one or more intervening voids 568 positioned therebetween. The support columns 566 provide structural support to the probe shaft 552 and facilitate the transmission of the compressive forces along the probe shaft 552 to the planar punch tip 554. Additionally, as described with FIG. 5A, the support columns 566 provide features having an overall cross sectional area less than the cross sectional area of the remainder of the probe shaft 552 (e.g., proximal to the voids 568 and the planar punch tip 554). The smaller cross sectional area of the support columns 566 cooperates with the materials of the mechanical testing instrument 550 (for instance having a low coefficient thermal expansion and thermal conductivity) to substantially retard or throttle heat transfer from the planar punch tip 554 proximally through the probe shaft 552. Additionally, the voids 568 retard or throttle heat transfer through the probe shaft 552 by providing a spaces or windows between portions of the probe shaft 552 for instance the proximal portions of the probe shaft and the planar punch tip 554 (as with the voids 518 shown in FIG. 5A).

Figure 5C:
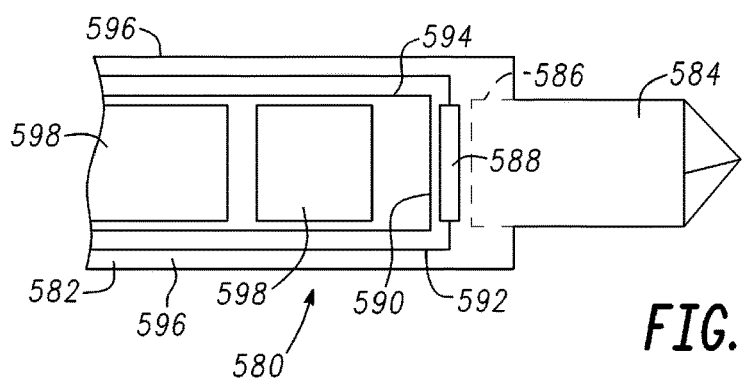
FIG. 5C is a top view of yet another example of a mechanical testing instrument configured for heating.

FIG. 5C shows yet another example of a mechanical testing instrument 580, for instance a mechanical testing instrument configured for indentation or scratching of the sample. As shown in FIG. 5C, the mechanical testing instrument 580 includes a probe shaft 582 and a probe tip 584 coupled with the probe shaft 582. In one example, the probe shaft 582 includes a shaft socket 586 sized and shaped to receive the probe tip 584 therein. In another example, the probe tip 584 is integrally formed with the probe shaft 582. As described above, the mechanical testing instrument 580 is shown in FIG. 5C is configured for indentation and scratching a sample, for instance a sample positioned within the sample gripping and heating assembly 102 shown in FIG. 1. In yet another example, the probe tip 584 has known and predictable tip geometry such as a Berkovich tip geometry.

The mechanical testing instrument 580 further includes in one example a heating element 588 and a sensing element 590 positioned within the probe shaft 582. In one example, the heating and sensing elements 588, 590 are positioned remotely relative to proximal portions of the probe shaft 582 according to positioning at the ends of support columns 596 with intervening voids 598 between the support columns 596. As described herein previously, the support columns 596 include cross sectional areas less than the cross sectional area of the remainder of the probe shaft 582, for instance those portions of the probe shaft 582 adjacent to the probe tip 584 and those portions proximal to the voids 598. The smaller cross sectional area of the support columns 596 substantially retards conductive heat transfer from the heating element 592 near the probe tip 584 to the proximal portions of the probe shaft 582. Additionally the one or more voids 598 are provided to further enhance the throttling of heat transfer from the heating element 588 to the proximal portions of the probe shaft 582 for instance remote from the probe tip 584. For instance, the voids 598 retard conductive heat transfer through the probe shaft 582 by instead directing heat transfer into the support columns 596. Additionally, by providing the voids 598 radiative heat transfer for instance across the voids 598 provides a further throttling of heat transfer along the probe shaft 582 as opposed to direct conduction of heat through the probe shaft 582.

The support columns 596 and the voids 598 cooperate with the materials of the mechanical testing instrument 580 (e.g., materials having low coefficients of thermal expansion and thermal conductivity) to retard or substantially eliminate heat transfer along the probe shaft 582 away from the heating element 588. Instead heat is generated and localized to the portion of the probe shaft 582 adjacent to the tip 584. The heating element 588 is thereby able to elevate the temperature of the probe tip 584 to a temperature approaching or identical to the elevated temperature of a sample, such as the sample 200 positioned within the sample gripping and heating assembly 102. As described above with regard to FIG. 5A (and similarly applicable to the mechanical testing instrument 550 shown in FIG. 5B), the elevation of the temperature of the probe tip 584 facilitates the mechanical testing of the sample 200 at an elevated temperature with substantially no heat transfer to or from the sample 200 that would otherwise raise or lower its temperature and thereby skew results for a testing procedure requiring heating of the sample. That is to say, where the sample is to be tested at a specified temperature, such as 1200° C., by heating the mechanical testing instrument 580 as well as the sample gripping and heating assembly 102 (and the sample 200 therein correspondingly) the engagement of the mechanical testing instrument 580 with the sample 200 results in substantially no heat transfer into or out of the sample 200. Instead the mechanical testing instrument 580 engages the sample 200 and maintains the sample at its elevated temperature (e.g., 1200° C.) while the probe tip 584 indents or scratches on the surface. The sample 200 is thereby maintained at the elevated temperature and observed at that elevated temperature with regard to its mechanical properties throughout the testing procedure.

Figure 6A:
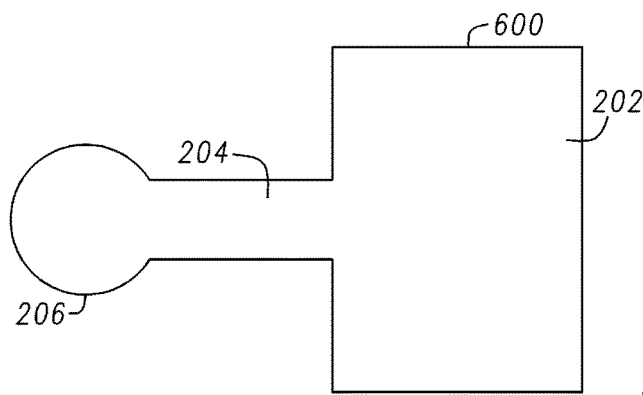
FIG. 6A is a top view of one example of a sample configured for at least tensile testing.

FIG. 6A-D show various examples of samples sized and shaped for use with the sample gripping and heating assembly 102. For instance, the samples are configured for positioning between and gripping with the heating grips 104 shown in FIG. 1. Referring first to FIG. 6A, the sample 200 previously shown in FIG. 2 is provided again. In this example, the sample 200 is shown before coupling with the gripping surfaces 300 of the heated grips 104. The sample 200 includes engagement surfaces 600 sized and shaped to provide surface to surface coupling with the gripping surfaces 300 of the heating grips 104. For instance, in one example, the engagement surfaces 600 provide flat surfaces sized and shaped to engage with the corresponding flat surfaces of the gripping surfaces 300. In another example, and as previously described herein, the engagement surfaces 600 are knurled, corrugated or have a surface roughening texture sized and shaped to facilitate continued surface to surface contact with the gripping surfaces 300 but further increases the frictional force between the gripping surfaces 300 and the engagement surfaces 600. Optionally the gripping surfaces 300 shown in FIGS. 3A and 3B include corresponding surface roughening, knurling, corrugations and the like to facilitate enhanced gripping of the sample 200 between the gripping surfaces 300.

Figure 6B:
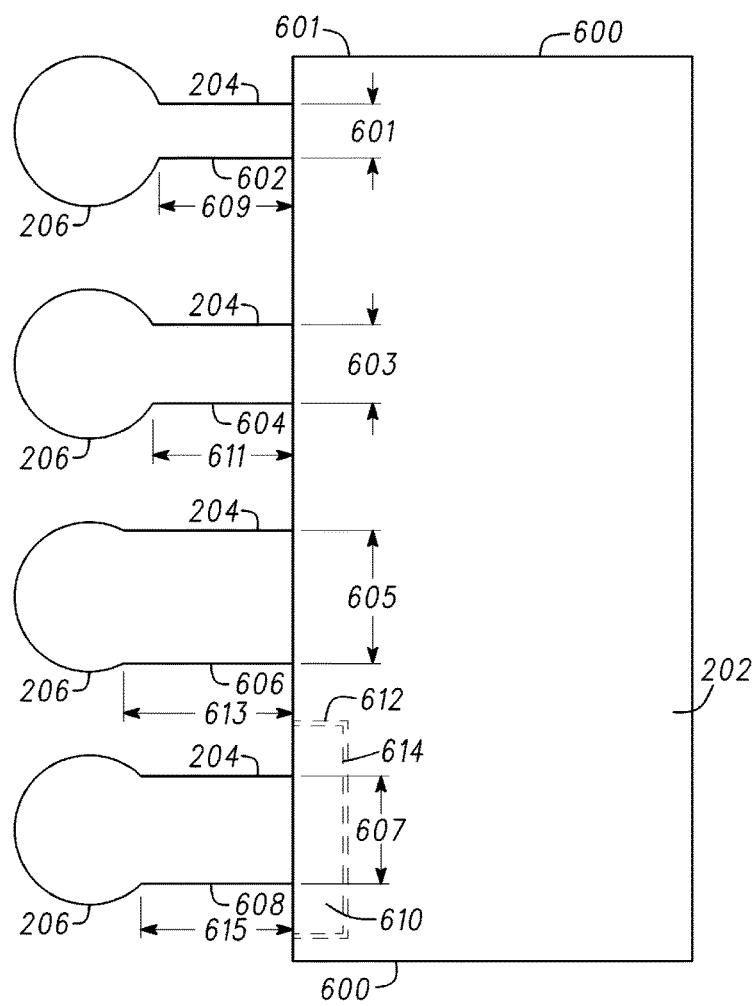
FIG. 6B is a top view of one example of a sample having multiple sample portions configured for at least tensile testing.

FIG. 6B shows another example of a sample 601 including first, second, third and fourth sample portions 602-608. As shown, the sample 601 includes a sample substrate 202 similar to the sample substrate 202 shown in FIG. 2. The sample substrate 202 includes a plurality of sample shafts 204 extending therefrom and extending to sample heads 606. In the example shown in FIG. 6B, the sample 601 includes the plurality of the first, second, third and fourth sample portions 602-608 configured for tensile testing. That is to say, the sample heads 206 are sized and shaped for gripping by the gripping probe 400 shown in FIG. 4A.

As shown in FIG. 6B, in some examples, at least the first, second and third sample portions 602-606 include varying dimensions on their respective sample shafts 204. For instance, the first, second and third sample portions 602-606 include corresponding sample widths 601-605. As shown, the sample widths 601-605 progressively enlarge from the first sample portion 602 through the second and third sample portion 604, 606. In one example, the sample 601 is sized and shaped to provide a variety of sample portions 602-608 having corresponding changes in one or more dimensions including width 601-607 or sample length 609-615. The change in dimensions of the sample portions 602-608 allows for testing of a sample constructed of a single or unitary material at various widths or lengths, for instance to measure the tensile modulus of each of the sample portions at elevated temperatures. In some examples, the mechanical characteristics of the first, second, third and fourth sample portions 602-608 vary according to one or more of the sample widths 601-607 or sample lengths 609-615 (and optionally further vary according to temperature).

The provision of multiple sample portions 602-608 on the sample 601 thereby facilitates the ready and rapid examination of each of the samples having the varying dimensions during a single testing procedure without breaking down and reinstalling multiple samples within the same testing fixture. For instance, the sample 601 is positioned between the heating grips 104 of the sample gripping and heating assembly 102. With the provision of a stage, such as a multiple degree of freedom stage (described herein), coupled with the high temperature sample testing system 100 shown in FIG. 1 each of the sample portions 602-608 may be moved sequentially into engagement with the gripping tip 404 shown in FIG. 4A to allow for the testing of each of the sample portions 602-608 without requiring the decoupling and installation of supplemental samples within the sample gripping and heating assembly 102.

In another example, the sample 601 includes one or more samples, such as the fourth sample portion 608, adhered with the sample substrate 202. As shown in one example, the fourth sample portion 608 includes a sample base 610 positioned within a sample socket 612 of the sample substrate 202. For instance, the sample base 610 is coupled with the sample socket 612 with an adhesive such as a high temperature adhesive configured to maintain adhesion of the fourth sample portion 608 with the sample substrate 202 at elevated temperatures, for instance, temperatures up to or above 1200° C. The provision of a sample portion such as the fourth sample portion 608 separate from the sample substrate 202 allows for the coupling of a sample portion having material different from the sample substrate 202. In this manner, an array of sample portions may be coupled with the single sample substrate 202 to facilitate the ready testing of multiple materials on a single substrate 202 when coupled with the sample gripping and heating assembly 102. In this regard multiple samples having multiple materials may be positioned at one time within the sample gripping and heating assembly 102 and thereafter tested in rapid succession by a mechanical testing instrument. In one example, the provision of a multiple degree of freedom stage allows for the flexible orientation and reorientation of the sample 601 relative to the mechanical testing instrument to facilitate the alignment of the sample portions 602-608 with the mechanical testing instrument without requiring the decoupling and the installation of various separate samples within the high temperature sample testing system 100.

In another example, the sample 601 including multiple sample portions 602-608 is formed of a unitary piece of material. In one example, each of the sample portions 602-608 are formed with one or more of a focused ion beam (FIB), ion milling, masking and etching and the like to form each of the first through fourth sample portions 602-608. As previously described herein the provision of multiple sample portions 602-608 on a single substrate allows for the testing and examination of multiple sample portions (for instance having differing sample dimensions such as the sample widths 601-607 and sample lengths 609-615).

Figure 6C:
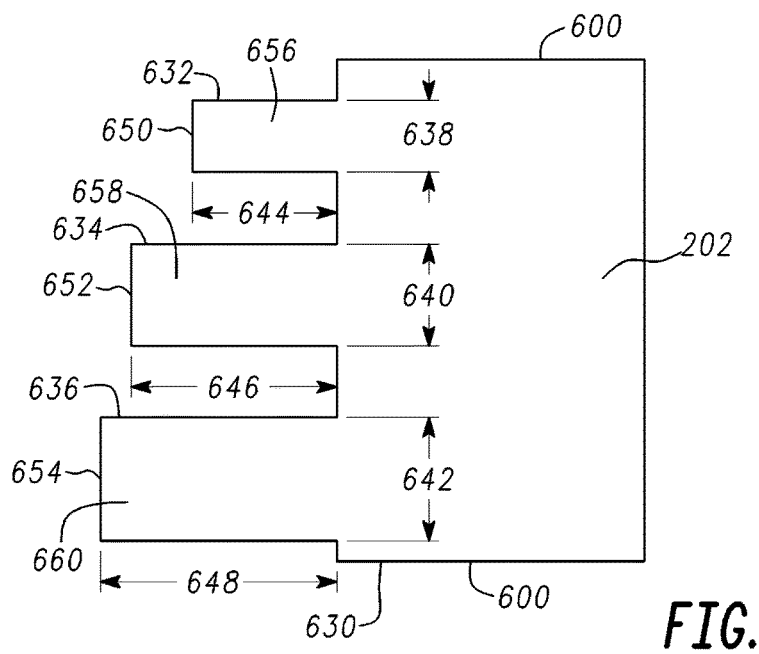
FIG. 6C is a top view of one example of a sample having multiple sample portions configured for at least compressive testing.

Referring now to FIG. 6C, another example of a sample 630 is provided. In the example shown in FIG. 6C the sample 630 is one example of a sample configured for compressive testing. The sample 630 includes a plurality of sample portions 632-636 (e.g., first, second and third sample portions). As with the previously described sample 601 the first, second and third sample portions 632-636 include one or more of differing sample widths and sample lengths 638-642, 644-648, respectively. In a similar manner to the first, second, third and fourth sample portion 602-608 shown in FIG. 6B, the sample portion 632-636 allow for the examination and testing of multiple sample portions with varying dimensions constructed of the same or differing materials and coupled with a single sample substrate 202.

FIG. 6C further shows that each of the sample portions 632-636 includes planar sample surfaces 650-654. The planar sample surfaces allow for the engagement of the plurality of sample portions in surface to surface contact with a mechanical testing instrument such as the mechanical testing instrument 550 shown in FIG. 5B having a planar punch surface 556. The engagement of the mechanical testing instrument 550 with the planar sample surfaces 650-654 allows for the testing and examination of compressive loads on each of the sample portions 632-636. As with the sample portions 602-608 shown in FIG. 6B the varying of one or more dimensions of the plurality of sample portions 632-636 allows for the examination and testing of the same or differing materials according to those dimensions on a single sample substrate 202, optionally at elevated temperatures according to operation of the sample gripping and heating assembly 102.

Additionally, by providing multiple sample portions 632-636 (or 602-608), the sample gripping and heating assembly 102 and the samples 630, 601 are heated at a single time and the sample portions are correspondingly heated according to that single step elevation of temperature for the sample portions. Stated another way, multiple instances of decoupling, installation and subsequent heating and reheating of samples is not required as each of the sample portions is provided on a single substrate 202 to allow for the heating and testing of the substrate 202 and the sample portions in a rapid and sequential manner as required by a testing procedure (e.g., a testing procedure that requires the testing of multiple samples at an elevated temperature).

As further shown in FIG. 6C, each of the sample portions 632-636 includes respective sample shafts 656-660. As shown in the example, each of the sample shafts 656-660 has varying sample lengths 644-648 and sample widths 638-642. With the provision of a multiple degree of freedom stage, for instance coupled with the stage interface 114 shown in FIG. 1, each of the sample shafts 656-660 may be oriented into alignment and surface to surface contact with an instrument such as the mechanical testing instrument 550 shown in FIG. 5B and configured for compressive testing. That is to say, the multiple degree of freedom stage is configured to orient each of the sample shafts 656-660 including for instance its longitudinal axis into alignment or coincidence with the corresponding axis and ensure surface to surface contact with the corresponding surfaces of the mechanical testing instrument. The multiple degree of freedom stage is thereby able to provide enhanced flexibility for rapid testing of multiple sample portions on a single sample substrate 202 despite the need for repositioning and reorientation of each sample portion relative to a testing instrument.

Figure 6D:
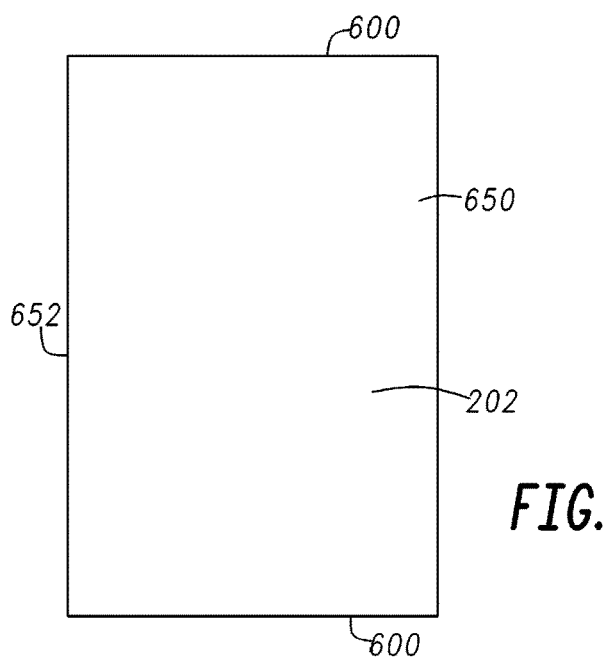
FIG. 6D is a top view of one example of a sample configured for at least one of indentation and scratch testing.

FIG. 6D shows yet another example of a sample 650. In this example, the sample 650 includes a planar sample surface 652 sized and shaped for one or more of indentation or scratching such as with the mechanical testing instrument 580 shown in FIG. 5C. For instance, the planar sample surface 652 provides a surface sized and shaped for reception of a probe tip 584. As with the other samples described herein, the sample 650 includes engagement surfaces 600 sized and shaped to engage with the gripping surfaces 300 of the heating grips 104 shown in FIG. 1. The engagement of the heating grips 104 along the engagement surfaces 600 fixes the sample substrate 202 of the sample 650 within the sample gripping and heating assembly 102 and fixes the sample 650 in place for testing of the sample, for instance through indentation or scratching by the probe tip 584 shown in FIG. 5C.

In each of the examples shown for the samples described in FIG. 6A-D the sample substrates 202 are substantially larger than the sample portions sized and shaped for testing (excepting the sample 650 without a sample shaft or sample head). Because the substrates 202 are relatively large the substrates in combination with the heat gripping assemblies 102 substantially fix any portion of the samples sized and shaped for testing. Stated another way, the sample substrates 202 provide a robust sample substrate that is resistant to deflection, compression or the like while the samples (e.g., sample portions or sample surface 652) are tested with any of the instruments described herein. Further, in the case of the sample 650 shown in FIG. 6D the planar sample surface 652 provides a localized area for testing while the remainder of the sample substrate 202 underlying the surface 652 and positioned between the engagement surfaces 600 provides a robust and substantial volume sized and shaped to support the planar sample surface 652, for instance during indentation and scratching of the planar sample surface.

Figure 7:
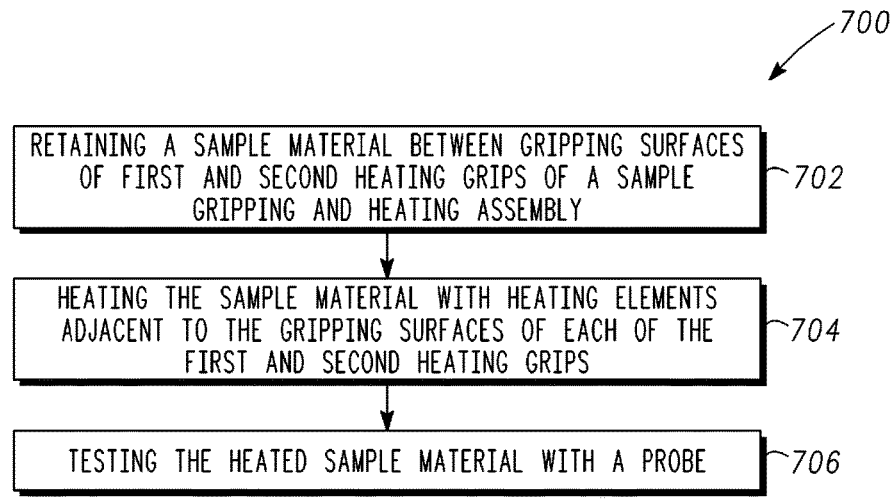
FIG. 7 is a block diagram showing one example of a method for mechanically testing a sample with a testing assembly includes a sample gripping and heating assembly.
Figure 9:
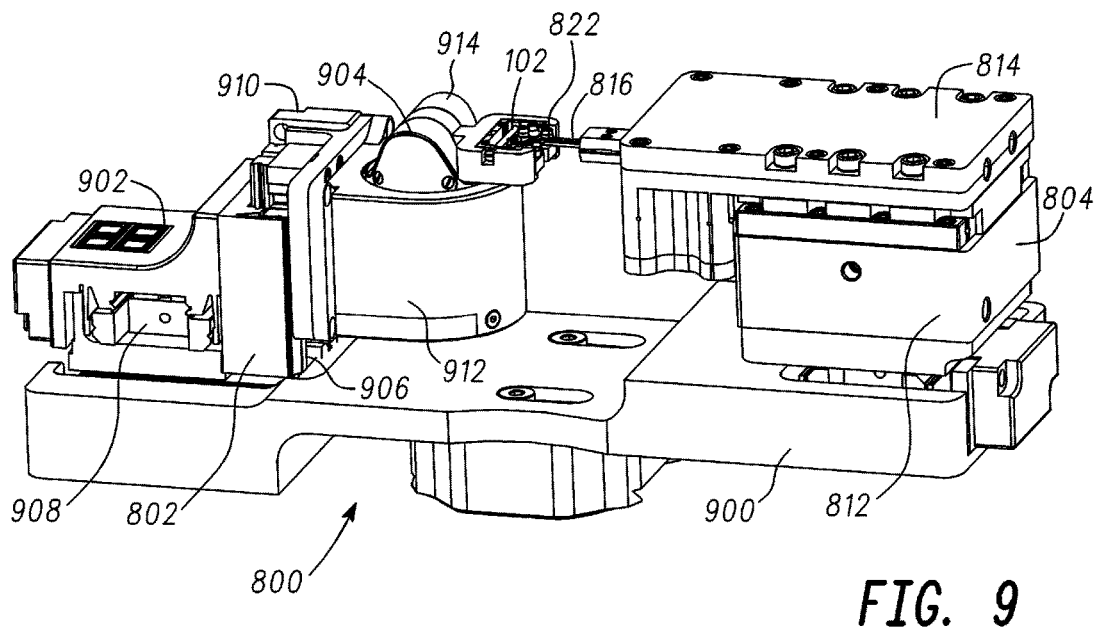
FIG. 9 is a perspective view of one example of a testing assembly including the sample gripping and heating assembly and a probe heater.

FIG. 7 shows one example of the method 700 for mechanically testing a sample at a scale of microns or less with a testing assembly such as the testing assembly 800 shown in FIGS. 8 and 9. In describing the method 700 reference is made to one or more components, features, functions and the like described herein. Where convenient reference is made to the components and features with reference numerals. Reference numerals provided are exemplary and are not exclusive. For instance, the features, components, functions and the like described in the method 700 include the corresponding numbered elements other corresponding features described herein (both numbered and unnumbered) as well as their equivalents.

At 702, the method 700 includes retaining a sample such as the sample 200 shown in FIG. 2 between gripping surfaces of first and second heating grips 104. As shown in FIG. 2, the first and second heating grips 104 are a part of the sample gripping and heating assembly 102. In one example, gripping the sample 200 includes deflecting the first and second opposed arms 113 as shown in FIGS. 1 and 2. Optionally, the sample gripping and heating assembly 102 is positioned within a gripping assembly socket 110 of a stage adaptor including a stage interface 114 configured for coupling with the stage, such as the stage 802 shown in FIG. 8.

At 704, the method 700 includes heating the sample 200 with heating elements such as the heating elements 302 adjacent to the gripping surfaces 300 of each of the first and second heating grips 104. Stated another way, at each of the interfaces with the sample 200 the gripping surfaces 300 including the heating elements 302 therein are positioned adjacent to the sample and thereby readily conduct heat to the sample 200. Optionally, heating of the sample by way of the sample gripping and heating assembly 102 includes controlling temperatures of the heating elements 302 of each of the first and second heating grips 104. Controlling the temperatures of the heating elements 302 optionally includes maintaining the temperatures substantially the same between the heating elements 302 of the heating grips 104. Stated another way, the temperatures at each of the heating elements 302 are controlled, for instance by a heater control module 828 shown in FIG. 8, to ensure that the temperatures at the heating elements 302 are substantially the same. A heat gradient across the sample 200 and corresponding heat transfer from the sample 200 to one of the heating grips 104 is thereby avoided.

In still another example the method 700 further includes heating the probe, such as the probe 816 shown in FIG. 8 with a probe heater 822 (or heating of any of the probes described herein with the respective probe heaters shown herein) in combination with heating of the sample 200 by way of the sample gripping and heating assembly 102. Optionally, heating of the sample 200 and the probe 816 is controlled for instance by the heater control module 828 to substantially ensure that the temperature of the sample and the probe are substantially the same prior to mechanical testing of the heated sample (e.g., one or more of engagement between the probe and the sample and testing of the sample).

At 706, the method 700 includes mechanically testing the heated sample 200 with a probe, such as the displaceable probe 822 shown in FIG. 8 or any of the other probes described herein. In one example, mechanically testing includes one or more of indentation, scratch or creep testing of the heated sample 200 with a probe, such as the probe tip 584 shown in FIG. 5C. In another example, mechanically testing the sample 200 includes one or more of compression testing or tensile testing of the sample with a probe. Optionally, compression testing is conducted with the planar punch tip 554 shown in FIG. 5B and tensile testing is conducted with the gripping tip 504 of the mechanical testing instrument 500 shown in FIG. 5A. In another example, mechanically testing the heated sample 200 includes mechanically testing a plurality of sample portions of the sample, for instance sample portions having separate sample shafts and sample heads of different or the same material but with different characteristics or dimensions.

FIG. 8 is a schematic block diagram illustrating an example of a testing assembly 800 including a stage 802, a transducer assembly 804 and a controller 806. The testing assembly 800 employs a heating system 808 for heating and sensing the temperature of a test sample 810. In one example, the transducer assembly 804 includes a flexural actuator 812 and a transducer 814, such as a multi-plate capacitor electro-mechanical transducer having a displaceable probe 816. The transducer includes, but is not limited to, indentation, compression, tensile, fatigue, tribology, fracture instruments and the like.

The testing assembly 800 further includes a stage 802, as described above. In one example, the stage 802 includes a multiple degree of freedom stage having one or more actuators configured to move the sample gripping and heating assembly 102 and a sample retained therein according to two or more degrees of freedom. As will be described herein, one example of a multiple degree of freedom stage includes a stage having translational, rotational and tilting degrees of freedom. The heating system 808 is configured for coupling with the stage 804 and the transducer by way of the sample gripping and heating assembly 102 and a probe heater 822. The multiple degree of freedom stage described herein is one example of a system that would benefit from the heating system 808. Additionally, the heating system 808 described herein is also configured for use with any mechanical, electro-mechanical or electrical testing assembly or instrument that would benefit from one or more of a heated sample or probe.

According to one embodiment, the controller 806 includes an input/output module 824, a transducer control module 826, a heater control module 828 for controlling operation of the heating system 808, a processor 830, such as microprocessor or digital signal processor (DSP) and/or field programmable gate array (FPGA), for example, and a memory system 832. According to one embodiment, the memory system 832 includes a displacement module 834, a force module 836, a temperature sensing module 838, and a heating module 840. According to another embodiment, the input/output module 824 further includes a D/A converter 842, and an A/D converter 844.

In one example, the computer 846 includes a processor 848 and a memory system 850 that stores an application module 852. The computer 846 may access and communicate with the controller 806 via an interface 854 (e.g. a USB interface). According to one embodiment, the application module 852, displacement module 834, and force module 836 each include instructions respectively stored in memories 832 and 850 and which are accessible and executable by the processor 830. The controller 806 is configured to control and monitor the movement of displaceable probe 816 (through one or more of the flexural actuator 812 or the transducer 814) and to provide data representative of a displacement of the displaceable probe 816 to the computer 846 through the interface 854. According to one embodiment, the controller 806 is configured to determine and adjust a force applied to the test sample 810 by the displaceable probe 816.

Additionally, the controller 806 is configured to control and monitor the temperature of the heating system 808 (including the sample gripping and heating assembly 102 and the probe heater 822) and the sample 810 and to provide data representative of a temperature of the heating system 808 and the sample 810 to the computer 846 via interface 854. In one example, the controller 806 is configured to determine and adjust a heating power 856 applied to the heating system 808 and the sample 810 to achieve a desired sample temperature for testing and observation of the sample. In one example, the controller 806 (e.g., the heater control module 858) uses the temperature signal 858 to adjust the heater power 856 to achieve the desired test subject temperature through one or more control methods including closed loop feedback control. In a similar manner, the heater power 860 for the probe heater 822 is adjusted by the heater control module 828 according to the temperature signal 862 provided from the probe heater. Optionally, the heater control module 828 ensures the heating system 808 including the sample gripping and heat assembly 102 and the probe heater 822 are operated cooperatively to achieve the same temperature at the displaceable probe 816 and the sample gripping and heating assembly 102 (e.g., at the interface of the heating grips 104 with the sample). That is to say, one or more of the sample gripping and heating assembly 102 and the probe heater 822 are actively heated to avoid passive unpredictable heating of a sample through heat transfer between the sample and the probe 816. Accordingly, there is minimal heat transfer through the sample 810 as the heated probe 816 contacts the heated sample 810 positioned retained in the sample gripping and heating assembly 102. By heating both the probe 816 and the sample 810, the heating system 808 is able to consistently and reliably test a sample 810 with the test assembly 800 without adversely altering the characteristics of the sample through unpredictable heat transfer caused by unheated components (e.g., the probe or the stage) in contact with the sample 810. Instead, the sample temperature and the probe temperature are adjusted through operation of the heating system 808 (controlled by the heater control module 828) to ensure the probe 816 is substantially the same temperature as the sample 810 at contact and throughout the testing procedure by way of active heating.

In operation, a user programs the controller 806 with the computer 846 through the application module 852. According to one embodiment, the controller 806, through the force module 836, provides an input or force signal to the transducer assembly 804 representative of a desired force for application to the test sample 810 by the displaceable probe 816. In response to the input actuation force signal, the transducer assembly 804 (one or more of the flexural transducer or the transducer) drives the displaceable probe 816 toward the sample 810. The displaceable probe 816 contacts and applies the desired force to the test subject 810. As will be described herein, displacement sensors are included in one or more of the transducer 814 and the flexural actuator 812. Optionally, the displacement sensor includes a transducer (e.g. a capacitive transducer) configured to detect movement of the displaceable probe 816 along at least one axis, and provides a displacement signal 866 to the controller 806 representing measurement of the movement of the displaceable probe 816. In other embodiments, in addition to movement along a single axis, the displacement sensors of one or more of the transducer 814 and the flexural actuator 812 detect and measure movement of the displaceable probe 816, such as displacement along one or more of the x, y or z axes or rotational movement about one or more of these axes. According to one embodiment, the testing assembly 800 further includes an imaging device 868 comprising an instrument such as an electron microscope, an optical microscope, or a scanning probe microscope (SPM) (e.g., an atomic force microscope (AFM)) configured to provide images of the sample 810 retained in the sample gripping and heating assembly 102, including one or more of images and video of the sample before, during and after mechanical testing such as indentation, compression, fatigue and fracture testing and the like.

For instance, test systems suitable for configuration with the heating system 808 include, but are not limited to, optical microscopes, scanning probe microscopes (SPM), electron microscopes and the like. In each of these examples, ex-situ or in-situ heating is performed with the heating system 808. Another test system suitable for configuration with the heating system 808 is an electron microscopy (e.g. one or more of transmission electron (TEM) or scanning electron (SEM)) in-situ nanomechanical tester commercially available under the trade name PicoIndenter from Hysitron, Incorporated, of Eden Prairie, Minn., USA.

During a temperature controlled mechanical testing, as will be described in greater detail below, the heating system 808 is controlled so as to heat and maintain the sample 810 at the desired temperature. The heating system 808 is operated with at least one of open loop control or closed loop control. For more accurate temperature regulation in a changing thermal environment, a closed loop control system utilizing the temperature signals 858, 862 as feedback are used. When the sample 810 temperature and the probe 816 temperature reach the desired temperature, the transducer assembly 804 is operated to apply a force with the moveable probe 816 to the sample 810. According to one embodiment, the temperature of the sample 810 is measured by the heating system 808 and the force applied and a displacement of the indented material of the sample 810 are measured by the testing assembly 800, as described herein. The force and displacement data and images of the corresponding deformation are substantially simultaneously measured in real-time and observed by a combination of the transducer assembly 804 (e.g. one or more displacements sensors) and the imaging device 868 (e.g., an electron microscope). Stated another way, examination of the test subject—through the above described measuring and imaging techniques—at a specified testing temperature is performed without any appreciable pause between deformation and measurement, imaging or heating. Observation and determination of these parameters and phenomena at or immediately after indentation are sometimes critical in the accurate assessment and determination of corresponding material properties.

Referring again to FIG. 8, the stage 802 is shown positioned relative to the displaceable probe 816. In one example, and as previously described herein the stage 802 includes a multiple degree of freedom stage having two or more degrees of freedom to position the sample gripping and heating assembly 102 with the sample 810 therein relative to the displaceable probe 816. In one example, the testing assembly is used in a larger overall instrument assembly, such as a scanning or transmission electron microscope or optical microscope. The positioning of the sample gripping and heating assembly 102 relative to the displaceable probe 816 allows for a variety of instruments of a larger overall instrument assembly to have access to the sample 810 while the sample is tested with the displaceable probe 816. Additionally, the orientation of the sample gripping and heating assembly 102 for instance by operation of two or more degrees of freedom of the stage 802 allows for testing of the sample 810 from a number of angles and orientations to thereby allow for scratching, indentation, creep, angled indentation testing and the like.

As shown in FIG. 8, the controller 806 includes a stage control module 870. In one example, the stage control module 870 is configured to provide an actuation signal 872 to the stage 802. The actuation signal 872, in one example, includes one or more component signals therein configured to operate the various stages of the stage 802. For instance, in one example, the stage 802 includes one or more of linear (translational), rotational and tilting stages. The actuation signal 872 accordingly has one or more components therein configured to operate each of the stages. In one example, the stage control module 870 provides instructions by way of the actuation signal 872 to the stage 802 according to a desired orientation input into the controller 806, for instance, by way of the computer 846. For a particular testing scheme the stage control module 870 moves the sample gripping and heating assembly 102 into a desired orientation (or orientations) to allow for access of the displaceable prove 816 to the sample 810 according to that desired orientation. In another example, the stage control module 870 allows for positioning and repositioning of the sample 810 for testing at multiple locations of the sample 810. For instance, where a plurality of test locations are distributed across the sample 810 (e.g., multiple sample shafts and heads) the stage 802 having a plurality of degrees of freedom is able to move the sample 810 into those orientations necessary for the displaceable probe 816 to have access to the testing locations.

As the stage 802 moves into the desired orientation according to the actuation signal 872, a position signal 874 for instance provided by one or more of encoders, potentiometers and other detection devices, is submitted to the controller 806 (e.g., the stage control module 870). In one example, the stage control module 870 is configured to index the position of the various stages of the stage 802 according to these position signals 874. For instance, in one example, the stage control module 870 uses a closed loop control system using the position signal 874 as feedback to ensure accurate and reliable positioning of the sample gripping and heating assembly 102 according to operation of the stage 802. The multiple degree of freedom stage described herein is one example of a system that would benefit from the heating system 808. Additionally, the heating system 808 (e.g., the sample gripping and heating system 102) described herein is also configured for use with any mechanical, electro-mechanical or electrical testing assembly or instrument that would benefit from one or more of a heated sample or probe.

FIG. 9 shows a perspective view of the testing assembly 800. As previously described, the testing assembly 800 includes a stage 802 and a transducer assembly 804. In the examples shown in FIG. 9, the stage 802 and the transducer assembly 804 are coupled with an assembly mount 900. The assembly mount 900 is configured in at least some examples to couple with a larger instrument assembly, for instance, the stage surface of one or more of a scanning electron microscope, an optical microscope or another instrument (e.g., a transmission electron microscope or other instrument with another configuration of the testing assembly 800).

As shown in FIG. 9, the transducer 804 has a flexural actuator 812 coupled with a transducer 814. In one example, the flexural actuator 812 is used to provide the displacement movement of the displaceable probe 816 while the transducer 814 is used to measure the corresponding movement of the displaceable probe 816 and forces incident upon the sample by way of engagement between the probe 816 and the sample during a testing procedure.

Referring again to FIG. 9, the stage 802 is shown having a plurality of degrees of freedom. For instance, the stage 802 includes in one example a linear stage assembly 902 coupled with an assembly mount 900. Optionally, the transducer assembly 804 is also coupled with the assembly mount 900. In another example, the stage 802 includes a rotation and tilt stage assembly 904 coupled in series with the linear stage assembly 902. The stage 802 has in one example two or more degrees of freedom to allow for positioning of the sample gripping and heating assembly 102 and the sample retained by the assembly relative to the displaceable probe 816. For instance, the linear stage assembly 802 includes first, second and third linear stages 906, 908, 910. The first, second and third linear stages 906, 908, 910 in one example correspond to the three Cartesian axes X, Y and Z. For instance, the first linear stage 906 corresponds to the Y axis, the second linear stage 908 corresponds to the X axis and the third linear stage 910 corresponds to the Z axis.

As further shown in FIG. 9, the rotation and tilt stage assembly 904 includes a corresponding rotational stage 912 coupled with a tilt stage 914. The sample gripping and heating assembly 102 is coupled with the tilt stage 914, for instance, by a spindle assembly adaptor (see the assembly socket 110 in combination with the stage interface 114 in FIG. 1) rotatably coupled with the remainder of the tilt stage 914. Coupling of the sample gripping and heating assembly 102 with the stage 802 allows for the positioning of a sample retained in the assembly 102 in any number of discrete orientations relative to the displaceable probe 816.

Additionally, and as will be described in further detail herein the heating system 808 is coupled with each of the displaceable probe 816 and the stage 802 in one example. For instance, the heating system 808 includes the sample gripping and heating assembly 102 configured to grip a sample, and the probe heater 822 is localized to the displaceable probe 816, for instance adjacent to a tip of the displaceable probe 816. The localized positioning and isolation of the heating system 808 including the component sample gripping and heating assembly 102 and the probe heater 822 allows for the rapid heating of a sample positioned between the heating grips 104 while at the same time allowing for mechanical testing of the sample without heat transfer between the heated sample and the heated displaceable probe 816.

Various Notes & Examples

Example 1 can include subject matter such as an apparatus, such as can include A testing assembly for use in material testing at a scale of microns or less, the testing system comprising: a heating system configured to heat a sample material and a probe, the heating system including: a gripping and heating assembly having first and second heating grips, each of the first and second heating grips including: a gripping surface, and a heating element adjacent to the gripping surface, the heating element configured to heat the sample material retained between the gripping surfaces; a probe heater having a probe heating element, the probe heater coupled with a probe configured for testing of the sample material retained between the gripping surfaces, the probe heater configured to heat the probe; a stage coupled with the sample gripping and heating assembly; and a transducer assembly coupled with the probe heater.

Example 2 can include, or can optionally be combined with the subject matter of Example 1, to optionally include a stage adaptor having a gripping assembly socket, and wherein the gripping and heating assembly is received within the gripping assembly socket, and the stage adaptor is coupled with the stage.

Example 3 can include, or can optionally be combined with the subject matter of one or any combination of Examples 1 or 2 to optionally include wherein the stage includes a multiple degree of freedom stage having at least one of rotation or tilt stages, and the stage adaptor is coupled with one of the rotation or tilt stages.

Example 4 can include, or can optionally be combined with the subject matter of one or any combination of Examples 1 through 3 to optionally include wherein the gripping and heating assembly includes a grip actuator coupled between the first and second heating grips, and the grip actuator is configured to move one or more of the gripping surfaces relative to the other gripping surface.

Example 5 can include, or can optionally be combined with the subject matter of one or any combination of Examples 1-4 to include wherein each of the first and second heating grips include a grip base and a base neck extending between the grip base and the gripping surface, and the base neck remotely positions the gripping surface from the grip base.

Example 6 can include, or can optionally be combined with the subject matter of Examples 1-5 to optionally include wherein the gripping and heating assembly includes a temperature sensing element adjacent to the gripping surface of each of the first and second heating grips.

Example 7 can include, or can optionally be combined with the subject matter of Examples 1-6 to optionally include wherein the gripping surfaces of the first and second heating grips are configured to reach temperatures of more than 400 degrees Celsius.

Example 8 can include, or can optionally be combined with the subject matter of Examples 1-7 to optionally include wherein the gripping surfaces of the first and second heating grips are configured to reach temperatures of more than 1100 degrees Celsius.

Example 9 can include, or can optionally be combined with the subject matter of Examples 1-8 to optionally include: at least one grip arm coupled with the first heating grip; and a grip actuator coupled with the at least one grip arm, and the grip actuator is configured to move the gripping surface of the first heating grip toward the gripping surface of the second heating grip and clamp sample material therebetween.

Example 10 can include, or can optionally be combined with any portion or combination of any one or more of Examples 1-9 to include subject matter than can include a gripping and heating assembly for testing including an assembly housing; a first heating grip coupled with the assembly housing; a second heating grip coupled with the assembly housing; and wherein the first and second heating grips each include: a gripping surface, and the gripping surfaces of the first and second heating grips are opposed to each other, and a heating element adjacent to the gripping surface.

Example 11 can include, or can optionally be combined with the subject matter of Examples 1-10 to optionally include a grip actuator coupled with the first and second heating grips, wherein the grip actuator is configured to move one or more of the gripping surfaces relative to the other gripping surface.

Example 12 can include, or can optionally be combined with the subject matter of Examples 1-11 to optionally include wherein the assembly housing is a clamping assembly having first and second opposed arms, and the first heating grip is coupled with the first opposed arm, and the second heating grip is coupled with the second opposed arm.

Example 13 can include, or can optionally be combined with the subject matter of Examples 1-12 to optionally include wherein a grip actuator extends between each of the first and second opposed arms, and the grip actuator moves the first and second opposed arms between initial positions and deflected positions, and in the deflected positions the gripping surfaces of the first and second heating grips are closer to each other than in the initial position.

Example 14 can include, or can optionally be combined with the subject matter of Examples 1-13 to optionally include wherein each of the first and second heating grips include a grip base and a base neck extending between the grip base and the gripping surface, and base neck remotely positions the gripping surface from the grip base.

Example 15 can include, or can optionally be combined with the subject matter of Examples 1-14 to optionally include a temperature sensing element adjacent to the gripping surface.

Example 16 can include, or can optionally be combined with the subject matter of Examples 1-15 to optionally include wherein the gripping surface of each of the first and second heating grips includes a tapered gripping surface, and the tapered gripping surfaces of the first and second heating grips are configured for engagement with corresponding tapered substrate surfaces of a sample.

Example 17 can include, or can optionally be combined with the subject matter of Examples 1-16 to optionally include wherein the gripping surface of each of the first and second heating grips includes a stepped gripping surface, and the stepped gripping surfaces of the first and second heating grips are configured for engagement with corresponding stepped substrate surfaces of a sample.

Example 18 can include, or can optionally be combined with the subject matter of Examples 1-17 to optionally include wherein the gripping surfaces of the first and second heating grips are configured to reach temperatures of more than 400 degrees Celsius.

Example 19 can include, or can optionally be combined with the subject matter of Examples 1-18 to optionally include wherein the gripping surfaces of the first and second heating grips are configured to reach temperatures of more than 1100 degrees Celsius.

Example 20 can include, or can optionally be combined with the subject matter of Examples 1-19 to optionally include a stage adaptor having a gripping assembly socket, and the assembly housing is received within the gripping assembly socket.

Example 21 can include, or can optionally be combined with any portion or combination of any one or more of Examples 1-20 to optionally include subject matter that can include a method of thermo-mechanical testing of a sample material at a scale of microns or less with a testing assembly including: retaining a sample material between gripping surfaces of first and second heating grips of a gripping and heating assembly; heating the sample material with heating elements adjacent to the gripping surfaces of each of the first and second heating grips; and testing the heated sample material with a probe.

Example 22 can include, or can optionally be combined with the subject matter of Examples 1-21 to optionally include wherein retaining the sample material includes gripping the sample material between the gripping surfaces of the first and second heating grips.

Example 23 can include, or can optionally be combined with the subject matter of Examples 1-22 to optionally include wherein gripping the sample material includes deflecting first and second opposed arms of an assembly housing, and the first heating grip is coupled with the first opposed arm and the second heating grip is coupled with the second opposed arm.

Example 24 can include, or can optionally be combined with the subject matter of Examples 1-23 to optionally include wherein the gripping surfaces include tapered gripping surfaces, and retaining the sample material includes engaging the tapered gripping surfaces with corresponding tapered substrate surfaces of the sample material.

Example 25 can include, or can optionally be combined with the subject matter of Examples 1-24 to optionally include wherein the gripping surfaces include stepped gripping surfaces, and retaining the sample material includes engaging the stepped gripping surfaces with corresponding stepped substrate surfaces of the sample material.

Example 26 can include, or can optionally be combined with the subject matter of Examples 1-25 to optionally include wherein heating the sample material includes controlling temperatures of the heating elements of each of the first and second heating grips, wherein the temperatures of the heating elements are substantially the same.

Example 27 can include, or can optionally be combined with the subject matter of Examples 1-26 to optionally include wherein heating the sample material includes throttling heat transfer from one of the first or second heating grip to the other of the second or first heating grip.

Example 28 can include, or can optionally be combined with the subject matter of Examples 1-27 to optionally include heating the probe; and controlling heating of the sample material and the probe to substantially the same temperature before testing the heated sample material.

Example 29 can include, or can optionally be combined with the subject matter of Examples 1-28 to optionally include wherein testing includes one or more of indentation testing or scratch testing of the heated sample material with the probe.

Example 30 can include, or can optionally be combined with the subject matter of Examples 1-29 to optionally include wherein testing includes one or more of compression testing or tensile testing of the sample material with the probe.

Example 31 can include, or can optionally be combined with the subject matter of Examples 1-30 to optionally include wherein the probe includes a gripping probe, and tensile testing of the sample material includes gripping the sample material with the gripping probe.

Example 32 can include, or can optionally be combined with the subject matter of Examples 1-31 to optionally include wherein the probe includes a planar punch probe, and compression testing of the sample material includes compressing the sample material with the planar punch probe.

Example 33 can include, or can optionally be combined with the subject matter of Examples 1-32 to optionally include wherein testing includes creep testing of the sample material with the probe.

Example 34 can include, or can optionally be combined with the subject matter of Examples 1-33 to optionally include wherein testing includes mechanical testing of the sample material with the probe.

Example 35 can include, or can optionally be combined with the subject matter of Examples 1-34 to optionally include wherein testing the heated sample material includes testing a plurality of sample portions of the sample material, the plurality of sample portions each including a sample shaft extending from a sample substrate.

Example 36 can include, or can optionally be combined with the subject matter of Examples 1-35 to optionally include inserting the sample gripping and heating assembly within a gripping assembly socket of a stage adaptor, and the stage adaptor is coupled with the stage.

Example 37 can include, or can optionally be combined with the subject matter of Examples 1-36 to optionally include wherein testing the heated sample material includes electrically testing the sample material with two or more electrical contacts in electrical communication with the sample material.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A testing assembly for use in material testing, the testing assembly comprising:
    a heating system configured to heat a sample material and a probe, the heating system including:
    a gripping and heating assembly having first and second heating grips, each of the first and second heating grips including:
        a gripping surface, and
        a heating element in the respective heating grip, the heating element adjacent to the gripping surface, the heating element configured to heat the sample material retained between the gripping surfaces;
    a probe heater having a probe heating element, the probe heater coupled with a probe configured for testing of the sample material retained between the gripping surfaces, the probe heater configured to heat the probe;
    a stage coupled with the gripping and heating assembly; and
    a transducer assembly coupled with the probe, the transducer assembly and the probe coupled with the stage.

2. The testing assembly of claim 1, further comprising a stage adaptor having a gripping assembly socket, and wherein the gripping and heating assembly is received within the gripping assembly socket, and the stage adaptor is coupled with the stage.

3. The testing assembly of claim 2, wherein the stage includes a multiple degree of freedom stage having at least one of rotation or tilt stages, and the stage adaptor is coupled with one of the rotation or tilt stages.

4. The testing assembly of claim 1, wherein the gripping and heating assembly includes a grip actuator coupled between the first and second heating grips, and the grip actuator is configured to move one or more of the gripping surfaces relative to the other gripping surface.

5. The testing assembly of claim 1, wherein the gripping and heating assembly includes a temperature sensing element adjacent to the gripping surface of each of the first and second heating grips.

6. The testing assembly of claim 1, wherein the gripping surfaces of the first and second heating grips are configured to reach temperatures of more than 400 degrees Celsius.

7. A method of thereto-mechanical testing of a sample material with a testing assembly comprising:
    retaining a sample material between gripping surfaces of first and second heating grips of a gripping and heating assembly including gripping the sample material between the gripping surfaces of the first and second heating grips;
    heating the sample material with heating elements at the gripping surfaces of each of the first and second heating grips, the heating elements coupled with the first and second heating grips, respectively, wherein heating the sample material with the heating elements includes conductively heating the sample material from the heating elements through the gripping surfaces; and
    testing the heated sample material with a probe.

8. The method of claim 7, wherein gripping the sample material includes deflecting first and second opposed arms of an assembly housing, and the first heating grip is coupled with the first opposed arm and the second heating grip is coupled with the second opposed arm.

9. The method of claim 7, wherein heating the sample material includes controlling temperatures of the heating elements of each of the first and second heating grips, wherein the temperatures of the heating elements are substantially the same.

10. The method of claim 7, wherein heating the sample material includes throttling heat transfer from one of the first or second heating grip to the other of the second or first heating grip.

11. The method of claim 7 comprising:
    heating the probe; and
    controlling heating of the sample material and the probe to substantially the same temperature before testing the heated sample material.

12. The method of claim 7, wherein testing includes one or more of indentation testing, compression testing, tensile testing or scratch testing of the heated sample material with the probe.

13. The method of claim 12, wherein the probe includes a gripping probe, and tensile testing of the sample material includes gripping the sample material with the gripping probe.

14. The method of claim 7, wherein testing includes mechanical testing of the sample material with the probe.

15. The method of claim 7, wherein testing the heated sample material includes electrically testing the sample material with two or more electrical contacts in electrical communication with the sample material.

\* \* \* \* \*